United States Patent
Arcuri et al.

(10) Patent No.: US 12,125,559 B2
(45) Date of Patent: Oct. 22, 2024

(54) PARALLELIZABLE SEQUENCE ALIGNMENT SYSTEMS AND METHODS

(71) Applicant: Samsung Electronics Co., Ltd., Suwon-si (KR)

(72) Inventors: Salvatore Arcuri, San Francisco, CA (US); Stephen Fischer, San Jose, CA (US); Vijay Balakrishnan, Mountain View, CA (US); Anahita Shayesteh, Los Altos, CA (US); Ramdas P. Kachare, Pleasanton, CA (US); Jason Martineau, Milpitas, CA (US); Yasser Zaghloul, San Mateo, CA (US)

(73) Assignee: SAMSUNG ELECTRONICS CO., LTD. (KR)

( * ) Notice: Subject to any disclaimer, the term of this patent is extended or adjusted under 35 U.S.C. 154(b) by 1169 days.

(21) Appl. No.: 16/551,712

(22) Filed: Aug. 26, 2019

(65) Prior Publication Data
US 2020/0364229 A1 Nov. 19, 2020

Related U.S. Application Data

(60) Provisional application No. 62/847,930, filed on May 14, 2019.

(51) Int. Cl.
*G16B 30/10* (2019.01)
*G06F 3/06* (2006.01)
*G16B 50/30* (2019.01)

(52) U.S. Cl.
CPC ............ *G16B 30/10* (2019.02); *G06F 3/061* (2013.01); *G06F 3/0658* (2013.01); *G06F 3/0679* (2013.01); *G16B 50/30* (2019.02)

(58) Field of Classification Search
CPC ............ G06F 16/24568; G06F 3/0604; G06F 3/0659; G06F 3/0679; G06F 3/061; G06F 3/0658; G06F 16/3346; G16C 20/20; G16B 30/10; G16B 35/00; G16B 50/30
See application file for complete search history.

(56) References Cited

U.S. PATENT DOCUMENTS 9,734,284 B2 * 8/2017 Olson et al.
9,845,552 B2 12/2017 Blume et al.
2017/0316154 A1 11/2017 Fitch et al.

OTHER PUBLICATIONS

Flannick J, Batzoglou S. Using multiple alignments to improve seeded local alignment algorithms. Nucleic Acids Res. Aug. 12, 2005; 33(14):4563-77. doi: 10.1093/nar/gki767. PMID: 16100379; PMCID: PMC1185574. (Year: 2005).*
N. Ahmed, K. Bertels and Z. Al-Ars, "A comparison of seed-and-extend techniques in modern DNA read alignment algorithms," 2016 IEEE International Conference on Bioinformatics and Biomedicine (BIBM), 2016, pp. 1421-1428, doi: 10.1109/BIBM.2016.7822731. (Year: 2016).*
Raj, Pethuru, et al. "High-performance big-data analytics." Computing Systems and Approaches (Springer, 2015) 1 (2015). (Year: 2015).*
Yoshimi, Masato, Celimuge Wu, and Tsutomu Yoshinaga. "Accelerating blast computation on an fpga-enhanced pc cluster." 2016 Fourth International Symposium on Computing and Networking (CANDAR). IEEE, 2016. (Year: 2016).*
Chen P, Wang C, Li X, Zhou X. Accelerating the Next Generation Long Read Mapping with the FPGA-Based System. IEEE/ACM Trans Comput Biol Bioinform. Sep.-Oct. 2014;11(5):840-52. doi: 10.1109/TCBB.2014.2326876. PMID: 26356857. (Year: 2014).*
Alachiotis, N., Berger, S., Flouri, T. et al. libgapmis: extending short-read alignments. BMC Bioinformatics 14 (Suppl 11), S4 (2013). https://doi.org/10.1186/1471-2105-14-S11-S4 (Year: 2013).*
Lin, Hao et al. "ZOOM! Zillions of oligos mapped." Bioinformatics (Oxford, England) vol. 24,21 (2008): 2431-7. doi:10.1093/bioinformatics/btn416 (Year: 2008).*
Recursion, Date Retrieved Mar. 19, 2024, https://en.wikipedia.org/wiki/Recursion, 11 Pages (Year: 2024).*

* cited by examiner

*Primary Examiner* — Larry D Riggs, II
*Assistant Examiner* — Kettip Kriangchaivech
(74) *Attorney, Agent, or Firm* — Renaissance IP Law Group LLP

(57) ABSTRACT

A field programmable gate array (FPGA) may: identify a continuous match of atoms between the search sequence and the reference sequence; divide the search sequence into a left portion of the search sequence that includes atoms before the continuous match of atoms in the search sequence, a center portion of the search sequence that includes the continuous match of atoms in the search sequence, and a right portion of the search sequence that includes atoms after the continuous match of atoms in the search sequence; match the left portion of the search sequence with the reference sequence; and match the right portion of the search sequence with the reference sequence.

22 Claims, 15 Drawing Sheets
Specification includes a Sequence Listing.

505

Genome 1: ATGCTATAGTAAATCTGCGCTAGCT

Genome 2: ATGCTATAGTAAATGTGCGCTAGCT

↑
Single Nucleotide Polymorphism

Deletion
↓

510

Genome 1: ATGCTATAGTAA--TCTGCGCTAGCT

Genome 2: ATGCTATAGTAAATCTGCGCTAGCT

↑
Insertion

Step 8

| A | C | T | G | A | T | T | C | A |   |   |
|---|---|---|---|---|---|---|---|---|---|---|
|   | A | C | G | C | A | T | C | C |   |   |
| 0 | 0 | 0 | 1 | 0 | 0 | 1 | 1 | 0 |   |   |

Weight = 8

Step 9

| A | C | T | G | A | T | T | C | A |   |   |
|---|---|---|---|---|---|---|---|---|---|---|
|   |   | A | C | G | C | A | T | C | C |   |
| 0 | 0 | 0 | 0 | 0 | 0 | 0 | 0 | 0 |   |   |

Weight = 7

Step 10

| A | C | T | G | A | T | T | C | A |   |   |
|---|---|---|---|---|---|---|---|---|---|---|
|   |   |   | A | C | G | C | A | T | C | C |
| 0 | 0 | 0 | 0 | 0 | 0 | 0 | 0 | 0 |   |   |

Weight = 6

Step 11

| A | C | T | G | A | T | T | C | A |   |   |
|---|---|---|---|---|---|---|---|---|---|---|
|   |   |   |   | A | C | G | C | A | T | C | C |
| 0 | 0 | 0 | 0 | 1 | 0 | 0 | 1 | 1 |   |   |

Weight = 5

Step 12

| A | C | T | G | A | T | T | C | A |   |   |   |
|---|---|---|---|---|---|---|---|---|---|---|---|
|   |   |   |   |   | A | C | G | C | A | T | C | C |
| 0 | 0 | 0 | 0 | 0 | 0 | 0 | 0 | 0 |   |   |   |

Weight = 4

Step 13

| A | C | T | G | A | T | T | C | A |   |   |   |
|---|---|---|---|---|---|---|---|---|---|---|---|
|   |   |   |   |   |   | A | C | G | C | A | T | C | C |
| 0 | 0 | 0 | 0 | 0 | 0 | 0 | 1 | 0 |   |   |   |

Weight = 3

Step 14

| A | C | T | G | A | T | T | C | A |   |   |   |
|---|---|---|---|---|---|---|---|---|---|---|---|
|   |   |   |   |   |   |   | A | C | G | C | A | T | C | C |
| 0 | 0 | 0 | 0 | 0 | 0 | 0 | 0 | 0 |   |   |   |

Weight = 2

Step 15

| A | C | T | G | A | T | T | C | A |   |   |   |
|---|---|---|---|---|---|---|---|---|---|---|---|
|   |   |   |   |   |   |   |   | A | C | G | C | A | T | C | C |
| 0 | 0 | 0 | 0 | 0 | 0 | 0 | 0 | 1 |   |   |   |

Weight = 1

FIG. 9B

SEQUENCE LISTING

```
<160> NUMBER OF SEQ ID NOS: 7

<210> SEQ ID NO 1
<211> LENGTH: 17
<212> TYPE: DNA
<213> ORGANISM: Unknown
<220> FEATURE:
<223> OTHER INFORMATION: Random nucleotide sequence

<400> SEQUENCE: 1
gctatcaccg taggtta                                              17

<210> SEQ ID NO 2
<211> LENGTH: 17
<212> TYPE: DNA
<213> ORGANISM: Unknown
<220> FEATURE:
<223> OTHER INFORMATION: Random nucleotide sequence

<400> SEQUENCE: 2
gttacagtgc atgcata                                              17

<210> SEQ ID NO 3
<211> LENGTH: 18
<212> TYPE: DNA
<213> ORGANISM: Unknown
<220> FEATURE:
<223> OTHER INFORMATION: Random nucleotide sequence

<400> SEQUENCE: 3
catacacgta gctatacg                                             18

<210> SEQ ID NO 4
<211> LENGTH: 44
<212> TYPE: DNA
<213> ORGANISM: Unknown
<220> FEATURE:
<223> OTHER INFORMATION: Random nucleotide sequence

<400> SEQUENCE: 4
gctatcaccg taggttacag tgcatgcata cacgtagcta tacg                44

<210> SEQ ID NO 5
<211> LENGTH: 25
<212> TYPE: DNA
<213> ORGANISM: Unknown
<220> FEATURE:
<223> OTHER INFORMATION: Random nucleotide sequence

<400> SEQUENCE: 5
atgctatagt aaatctgcgc tagct                                     25

<210> SEQ ID NO 6
<211> LENGTH: 25
<212> TYPE: DNA
<213> ORGANISM: Unknown
<220> FEATURE:
```

```
<223> OTHER INFORMATION: Random nucleotide sequence

<400> SEQUENCE: 6
atgctatagt aaatgtgcgc tagct                                              25

<210> SEQ ID NO 7
<211> LENGTH: 24
<212> TYPE: DNA
<213> ORGANISM: Unknown
<220> FEATURE:
<223> OTHER INFORMATION: Random nucleotide sequence

<400> SEQUENCE: 7
atgctatagt aatctgcgct agct                                               24
```

PARALLELIZABLE SEQUENCE ALIGNMENT SYSTEMS AND METHODS

RELATED APPLICATION DATA

This application claims the benefit of U.S. Provisional Patent Application Ser. No. 62/847,930, filed May 14, 2019, which is incorporated by reference herein for all purposes.

This application is related to co-pending U.S. patent application Ser. No. 16/435,442, filed Jun. 7, 2019, which claims the benefit of U.S. Provisional Patent Application Ser. No. 62/733,077, filed Sep. 18, 2018, and U.S. Provisional Patent Application Ser. No. 62/818,096, filed Mar. 13, 2019, and which is a continuation-in-part of U.S. patent application Ser. No. 16/260,087, filed Jan. 28, 2019, which is a continuation-in-part of U.S. patent application Ser. No. 16/226,629, filed Dec. 19, 2018, which is a continuation of U.S. patent application Ser. No. 16/207,080, filed Nov. 30, 2018, which claims the benefit of U.S. Provisional Patent Application Ser. No. 62/745,261, filed Oct. 12, 2018, all of which are incorporated by reference herein for all purposes.

REFERENCE TO AN ELECTRONIC SEQUENCE LISTING

The contents of the ASCII text file of the sequence listing named "1535-474_Sequence_Listing_ST25" which is 2 kb in size was created on Nov. 22, 2019, and electronically submitted via EFS-Web on Nov. 27, 2019, is herein incorporated by reference in its entirety.

FIELD

The inventive concepts relate generally to computer systems, and more particularly to pattern matching with inexact matches, such as in deoxyribonucleic acid (DNA) sequences.

BACKGROUND

One part of bioinformatics includes DNA sequence analysis. DNA sequencing may include comparing millions of DNA sequences of lengths between (typically) 30 to 100 nucleotides, with nucleotide sequences or parts of nucleotide sequences that can be billions of nucleotides long.

Conventional algorithms that may be used for this analysis include linear programming methods that may be used to find the optimal path within a matrix constructed by computing all cells of the matrix sequentially and then tracing back the paths from the cell that reached the highest score (e.g., in the Smith-Waterman algorithm) or from the cell at the lower right corner of the matrix (e.g., in the Needleman-Wunsch algorithm).

Although these algorithms may match sequences by predicting single nucleotide polymorphisms (SNPs) and insertions-and-deletions (indel) variations, they may be difficult to implement with acceleration techniques at least because the operations may be required to occur sequentially.

Accordingly, a need remains to perform DNA sequencing analysis with increased efficiency.

BRIEF DESCRIPTION OF THE DRAWINGS

FIGS. 9A-9B show examples of various weights being applied to the steps of a comparison of a search sequence and a reference sequence, according to an embodiment of the inventive concept.

Figure 1:
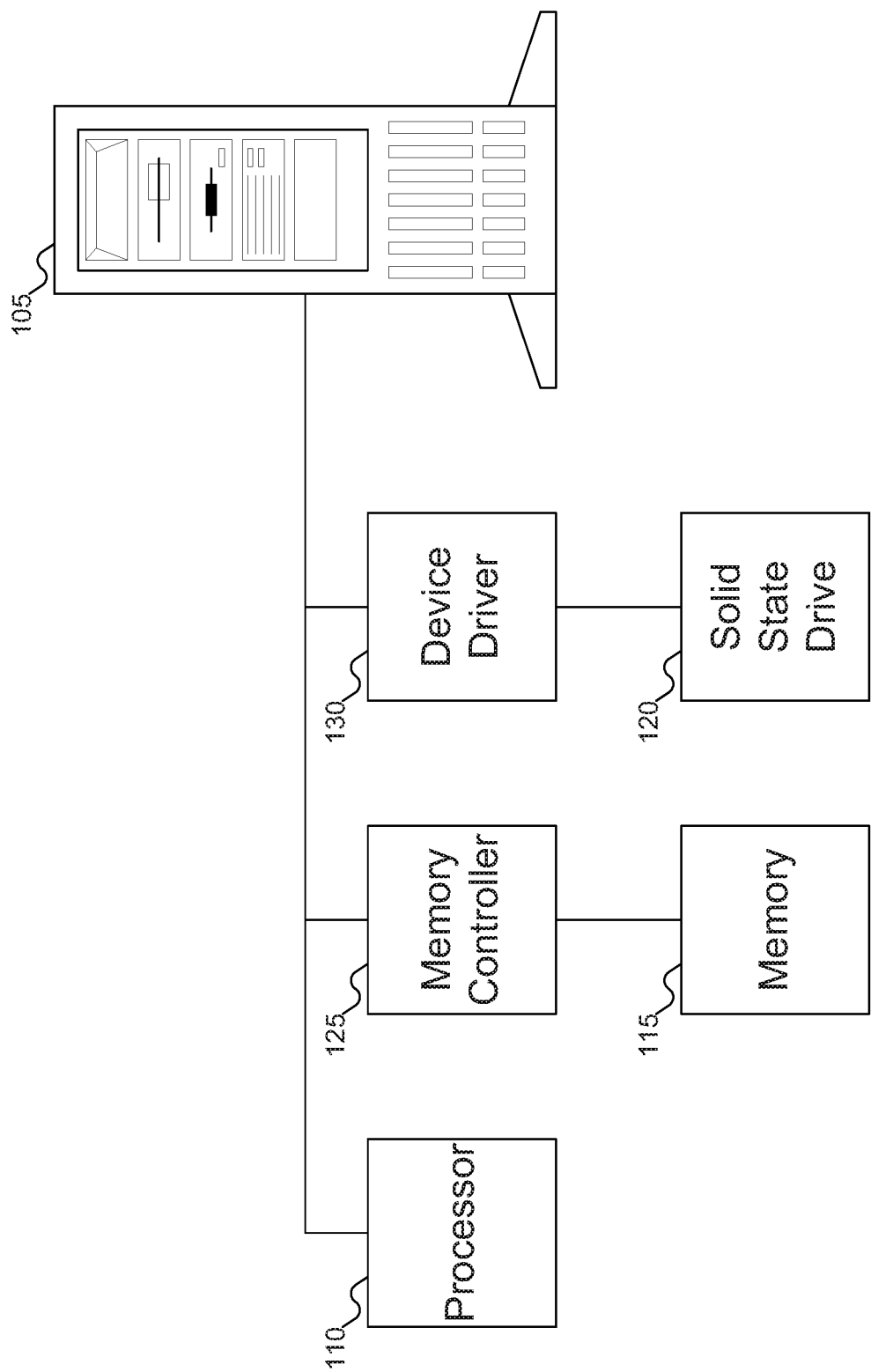
FIG. 1 shows a machine designed to support DNA sequencing and other analyses supporting parallel analysis, according to an embodiment of the inventive concept.

The figures are not necessarily drawn to scale. Elements of similar structures or functions are generally represented by like reference numerals for illustrative purposes throughout the figures. The figures are only intended to facilitate the description of the various embodiments of the inventive concept described herein. The figures do not describe every aspect of the teachings disclosed herein and do not limit the scope of the claims.

DETAILED DESCRIPTION

Reference will now be made in detail to embodiments of the inventive concept, examples of which are illustrated in the accompanying drawings. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first module could be termed a second module, and, similarly, a second module could be termed a first module, without departing from the scope of the inventive concept.

The terminology used in the description of the inventive concept herein is for the purpose of describing particular embodiments only and is not intended to be limiting of the inventive concept. As used in the description of the inventive concept and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The components and features of the drawings are not necessarily drawn to scale.

To provide parallelization of the computation to align sequences, embodiments of the inventive concept may slide sequences against each other, similar to the computation of a cross-correlation or a convolution. Multiple sliding steps may be performed in parallel, comparing and identifying the longest contiguous sequence of matches.

Once the longest sequence of matches is found, the corresponding elements of the two strings may be selected. This leaves up to two left fragments and up to two right fragments to be matched. The process is repeated on the left fragments and on the right fragments until no matches are found.

Consider comparing two sequences, such as nucleotides in deoxyribonucleic acid (DNA). The sequence to be analyzed may be slid against the larger sequence used as a reference.

Although the term steps, or sliding steps, may be used, these comparisons may be done in parallel. At every sliding step a string may be built. This string may be termed a score string, and may contain a 1 in the positions where the two sequences have the same type of nucleotide and a 0 where they have different types of nucleotide. Therefore, a 1 stands for match and a 0 for mismatch. The number of consecutive ones in the score string may be counted, restarting from zero every time there is a gap. In this manner, the largest number of consecutive ones may be identified.

The sequence of nucleotides in correspondence of these largest sequence of ones may be selected, which may be termed the matching sequence, may be stored for future use. The remaining sequence of nucleotides to the left of this matching sequence on each of the original sequences, if they exist, may be stored for future use too. Similarly, the remaining sequences of nucleotides to the right of the matching sequence on each of the original strings may be stored also for future use.

The process may then be repeated, but instead of using the original sequences, one process may use the left subsequences, and another process may use the right subsequences.

Favoring Alignments Using Weights

It is possible that the longest subsequence of is occurs in the early steps just after starting to slide the two sequences against each other, or near the end just before ending to slide the two sequences against each other. By focusing solely on the longest sequences of 1s, other matches may be overlooked in some cases that, while they may be not the longest sequence of matches, might cumulatively represent a better overall match.

To overcome this problem, rather than simply counting the number of matches, each match may be weighted, so that matches that are farther from the ends may be weighted more heavily. The weights may be assigned in such a way that the highest weight occurs when the centers of the two sequences are aligned, or when the left sides of the two sequence are aligned, or when the right sides of the two sequences are aligned, or when the two sequences are aligned at the position where the cross correlation between the two sequences is maximum, and decreasingly smaller weights as the matches are farther from these places of maximum weight.

The weight distribution could be made in two different ways:

1. Weights may depend on the distance from these positions of maxima (left, center, or right of the reference string) for each match, so that for a given step each position may have a different weight; or
2. The weights for all the locations may be the same for a given step, but varying from steps to steps, such that the steps that produce greater shifts from the positions of maxima generate smaller weight and the steps that produce smaller shifts from the positions of maxima generate larger weights, but for a given step all positions may have the same weight.

The process may be organized as a binary tree. The sequences may be considered text strings containing only four types of characters, A, T, C, and G. Unlike an ASCII text string requiring eight bits per character, to encode these sequences two bits per characters may be sufficient. Two bit comparators may be sufficient to determine if two nucleotides match or do not match.

Each node of the tree receives the two strings. Each node of the tree may generate a match string, up to two left substrings and up to two right substrings. If it generates a match and at least one left substring a left node is built. If it generates a match and at least one right substring a right node is built. The generation of new nodes may continue until there are no more nodes that produce matches with at least one substring.

Once the tree is built, it may be traversed in-order, in order to assemble two matched sequences, corresponding to the two original sequences. The construction of the two matched subsequences starts from the left most node in the tree. The matched sequences grow as the tree is traversed. In the places where the match exists, the matching nucleotides symbols may be inserted. In the places where the matches do not exist, the shorter of the two subsequences is extended with dashes (-) to match the length of the longer subsequence, to indicate a deletion. The so-modified subsequences may be appended to the corresponding matched sequence and cause them to grow.

In the places where the two strings have different characters, a single nucleotide polymorphism (SNP) may have occurred. In the places where the string corresponding to the string to be analyzed has a dash, a deletion may have occurred. In the places where the string corresponding to the reference string has a dash and the string corresponding to the string to be analyzed has a character an insertion may have occurred.

The nodes of the tree may be labeled with a unique ID consisting of a binary sequence of 0s and 1s. The length of this sequence may grow by one digit at every level of the tree. The ID of the root node may contain only one digit set it to 0. At every level the ID of the new node may extend the ID of its parent by one digit, appending a 0 if the new node is a left node or a 1 if the new node is a right node. The determination of whether a node is a left node or a right node may depend on the substrings being considered. If the two substrings that became the input strings to the new node were at the left of the matched sequence in the parent node then the new node is a left node. If they were at the right of the matched sequence in the parent node then the new node is a right node.

When the algorithm is used without weights, at each step it may be expected that the segment containing the most matches will be selected. But when the search is performed using weights, the weights may affect the outcome of the algorithm. For example, a match of 8 bases with a weight of 4 has a total score of 32, whereas a match of 7 bases with a weight of 5 has a total score of 35. To avoid a local maximum from preventing the algorithm from identifying the global maximum, the algorithm may also select some lower scoring matches in addition to the highest scoring match, and perform parallel searches based on those sub-optimal matches. In other words, parallelism may be used to investigate paths of the search tree that might otherwise be pruned by only selecting a single path through the search tree.

Parallelizable sequence alignment vs. cross-correlation and convolution A measure of the similarity between two functions, or two sequences in case of the discrete domain, may be given by the cross correlation between the two functions or two sequences. Cross correlation between two discrete sequences A[m] and B[m], where A and B may be two integer or real numbers, is defined as a function C[n] obtained by sliding the two sequences one against the other by an amount n and adding together the products obtained by multiplying the corresponding elements of A[m] and B[m].

The formula for the discrete cross correlation is the following:

$$C[n] = \sum_{m=-\infty}^{m=\infty} A[m] \times B[m-n]$$

Cross correlation is therefore a function that may have different values for different sliding positions. It may have relative maxima and minima. It indicates the degree of similarity of the two sequences. The maxima indicate the sliding positions that produce the maximum similarity. Thus one indication of where two sequences match the best may be obtained by computing the cross correlation of the two sequences, or which is the same counting the number of matches for each sliding position.

Cross correlation may be used between two sequences of nucleotides by defining the product as 1 when two nucleotides are of the same type and 0 when the two nucleotides are of different type. Therefore cross correlation may represent the number of matches as a function of the number of sliding steps.

A function that gives the number of matches for each sliding step may include the cross correlation function between the two sequences. The best match may be found where the cross correlation has the maximum value.

The disclosed system and method does not rely on the correlation function. The disclosed system and method does not count all the matches in a certain step; rather, the disclosed system and method may count the number of consecutive matches within a certain step, each multiplied but a weight function, and pick the consecutive run that produces the maximum value. The correlation may be used to find the step that produces the best alignment. The disclosed system and method may further use the information provided by the correlation function to determine where the maximum weight should be located, so that weights may be reduced as we move away from the point of maximum correlation.

Cross correlation may be considered, in certain aspects, to be similar to convolution. One difference may be that for the computation of the convolution one of the functions is flipped horizontally before sliding it against the other. That means that the independent variable m of one of the two functions is negated, as in the following formula:

$$C[n] = \sum_{m=-\infty}^{m=\infty} A[m] \times B[n-m]$$

The negation of the variable n does not transform the correlation into convolution or vice-versa, but it simply flips the result horizontally.

So far, this disclosure has discussed the application of the algorithm to sequence alignment for DNA. But the disclosed system and method may be used adjusted for other purposes as well.

Take, for example, protein sequences. Protein sequences may include long strings where each position in the string is occupied by one of 20 different amino acids. However, amino acids are different from nucleic acids in DNA; amino acids have a variety of chemical and structural features, such that when some amino acids replace with others, the effect can be to create either a substantially different protein, or a very similar protein, or anything in between, depending on the replacement. Thus, a sequence alignment in the protein space should be done not simply based on finding identical matches, but also finding chemically similar matches, and weighting them according to a level of similarity.

The disclosed system and method may be modified to match amino acid sequences accounting for the possibility that different amino acids might perform similar functions. The binary 1s and 0s (match or not) in the alignment scoring phase may be replaced with a multi-value system based on chemical or functional similarity, such as a block substitution matrix (BLOSUM) or point accepted mutation (PAM) matrixes. Such multi-value systems may be normalized to a 0-1 range. In terms of hardware implementations some changes may need to be made. For example, instead of using 2 bits of memory and 2 bit comparators as with DNA sequences, proteins may be analyzed with only one or a few more bits of memory/comparator (20 amino acids requires 5 bits to store; the weights, depending on the granularity, may be stored in 3 bits).

Further, the disclosed system and method may be used to find alignments between any sequence of "units" based on not just identity, but similarity, as long as the user provides a similarity matrix for the possible units. These base units may be letters, pixels, or other units that may be compared.

For example, one may generate a "similarity global regular expression print (GREP)" using the disclosed system and method where similar, but not matching, texts are found, and where the level of mismatch may be judged on a matrix indicating the likelihood of a "typo". As a further example, a search string of "firce", it may be evaluated as similar to a text of "force" since a typo-error matrix may be devised that recognizes that "o" is near "i" on the keyboard, and score accordingly. Meanwhile, "farce" may score comparatively less highly in an alignment, since a matrix for typos may recognize that "o" and "a" are distant.

As an alternate example, sequences of pixels may be compared with a weighted alignment matrix based on distance in a color/intensity chart. This may allow for a quick identification and comparison of images for overall similarity.

Finally, the disclosed system and method may be used for in-storage compute, particularly SSDs with onboard field programmable gate arrays (FPGAs). The disclosed system and method may be optimized for parallelization, and can be used across the units of the FPGA. If that FPGA is joined with an SSD, then data access times may be minimized (since there is no overhead of a managing host), and data throughput may be increased (since there is no software stack or external input/output (I/O) channel (e.g., Peripheral Component Interconnect Express (PCIe) or Ethernet) overhead), so the use of the FPGA parallelisms of the algorithm may be increased.

FIG. 1 shows a machine designed to support DNA sequencing and other analyses supporting parallel analysis, according to an embodiment of the inventive concept. In FIG. 1, machine 105 is shown. Machine 105 may include processor 110. Processor 110 may be any variety of processor: for example, an Intel Xeon, Celeron, Itanium, or Atom processor, an AMD Opteron processor, an ARM processor, etc. While FIG. 1 shows a single processor 110 in machine 105, machine 105 may include any number of processors, each of which may be single core or multi-core processors, and may be mixed in any desired combination.

Machine 105 may also include memory 115. Memory 115 may be any variety of memory, such as flash memory, Dynamic Random Access Memory (DRAM), Static Random Access Memory (SRAM), Persistent Random Access Memory, Ferroelectric Random Access Memory (FRAM), or Non-Volatile Random Access Memory (NVRAM), such as Magnetoresistive Random Access Memory (MRAM) etc. Memory 120 may also be any desired combination of different memory types. Memory 120 may be managed by memory controller 125.

Machine 105 may also include solid state drive (SSD) 120, which may be controlled by device driver 130. SSD 120 may be used to store data accessed by machine 105. For example, when machine 105 is used for DNA sequence analysis, SSD 120 may store the DNA sequences. Although the description below focuses on using SSD 120 for data storage, embodiments of the inventive concept may include other storage media as appropriate, such as hard disk drives or memory 115. SSD 120 may also be a Key-Value SSD (KV-SSD), where data is stored in objects that may be accessed via keys: when the KV-SSD receives a key, the KV-SSD may map that key to the location where the object is stored to read the data (or to write, update, or invalidate data, as appropriate to the request).

Although FIG. 1 depicts machine 105 as a server (which could be either a standalone or a rack server), embodiments of the inventive concept may include machine 105 of any desired type without limitation. For example, machine 105 could be replaced with a desktop or a laptop computer or any other machine that may benefit from embodiments of the inventive concept. Machine 105 may also include specialized portable computing machines, tablet computers, smartphones, and other computing machines.

Figure 2:
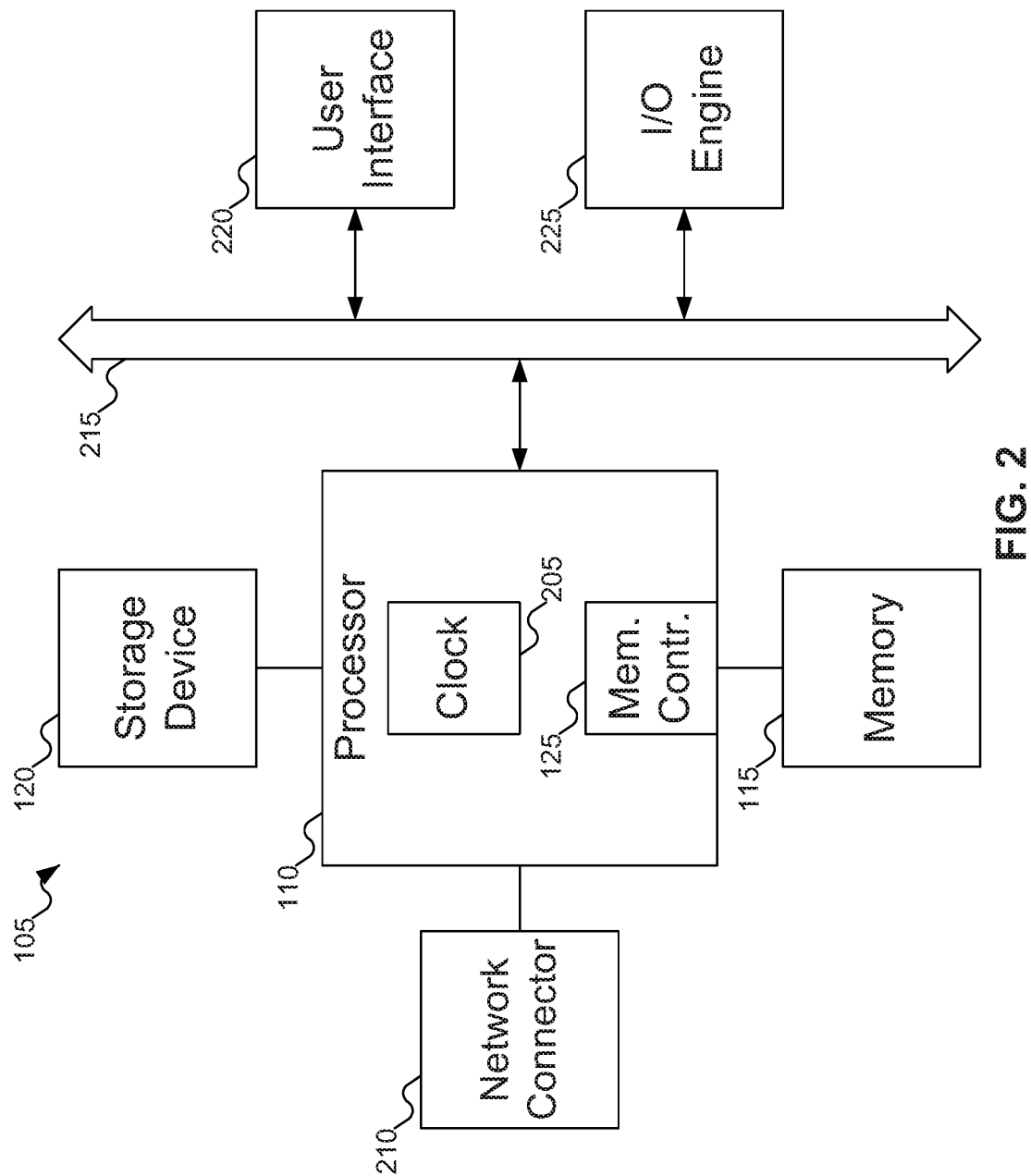
FIG. 2 shows some additional details of the machine of FIG. 1.

Embodiments of the inventive concept may be implemented using machine 105 (or parts therein). For example, embodiments of the inventive concept may perform sequence analysis implemented as software running on processor 110. Or, embodiments of the inventive concept may be implemented in part or entirely using a special-purpose processor, such as a field programmable gate array (FPGA) or an application-specific integrated circuit (ASIC) that may be used in machine 105. Or, embodiments of the inventive concept may be implemented within SSD 120 (again, either as software running on a general purpose processor in SSD 120 or using a special-purpose processor in SSD 120). FIG. 2 shows additional details of the machine of FIG. 1. In FIG. 2, typically, machine 105 includes one or more processors 110, which may include memory controllers 125 and clocks 205, which may be used to coordinate the operations of the components of machine 105. Processors 110 may also be coupled to memories 115, which may include random access memory (RAM), read-only memory (ROM), or other state preserving media, as examples. Processors 110 may also be coupled to storage devices 120, and to network connector 210, which may be, for example, an Ethernet connector or a wireless connector. Processors 110 may also be connected to buses 215, to which may be attached user interfaces 220 and Input/Output interface ports that may be managed using Input/Output engines 225, among other components.

Figure 3:
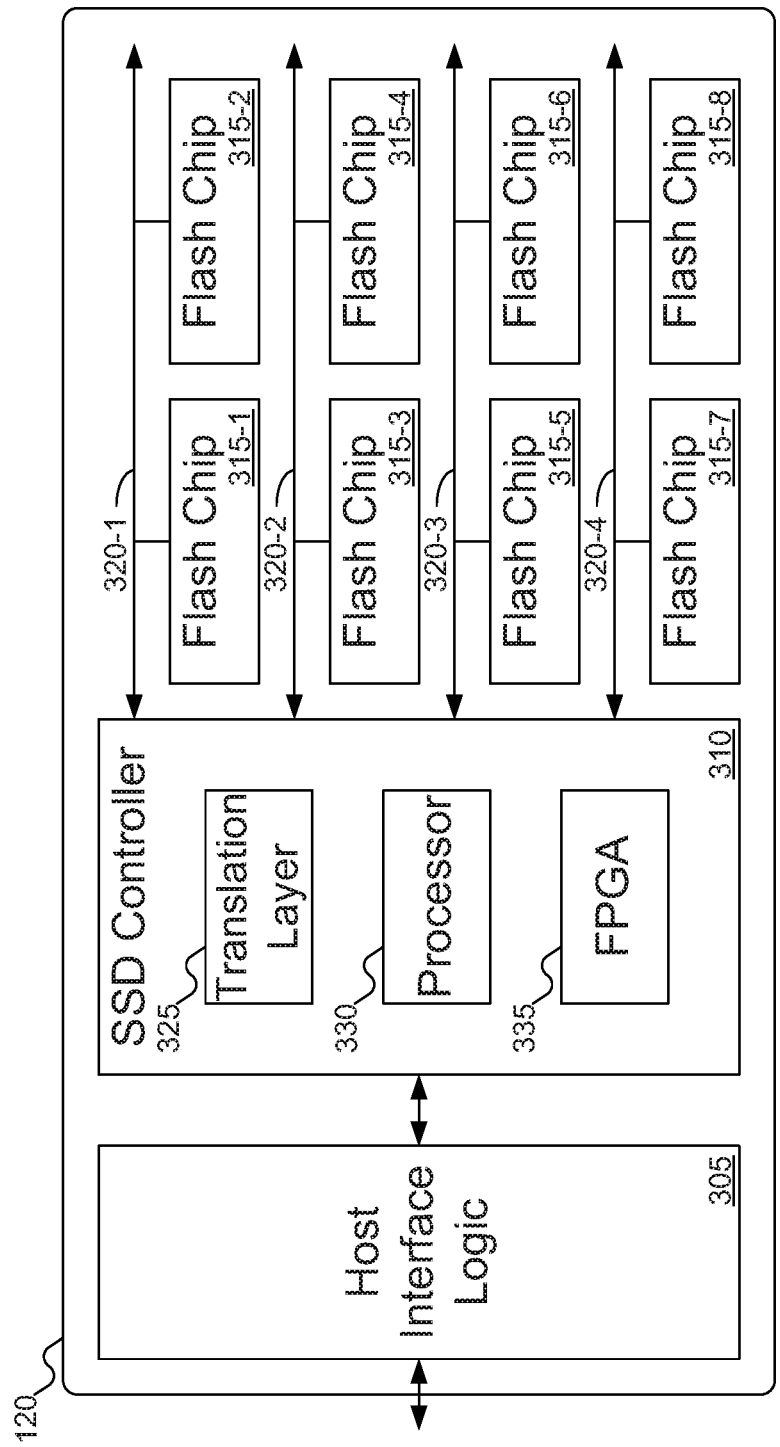
FIG. 3 shows some additional details of the solid state drive (SSD) of FIG. 1.

FIG. 3 shows details of solid state drive (SSD) 120 of FIG. 1. In FIG. 3, SSD 120 may include host interface logic 305, SSD controller 310, and various flash memory chips 315-1 through 315-8, which may be organized into various channels 320-1 through 320-4. Host interface logic 305 may manage communications between SSD 120 and machine 105 of FIG. 1. SSD controller 310 may manage the read and write operations, along with garbage collection and other operations, on flash memory chips 315-1 through 315-8.

SSD controller 310 may include translation layer 325. Translation layer 325 may perform the conventional functions of translating logical block addresses (LB As) into physical block addresses (PBAs) where the data is actually stored. In this manner, machine 105 of FIG. 1 may use its own address space to reference data, without having to know the physical addresses on SSD 120 where the data is actually stored. This may be beneficial when, for example, data is updated: since SSD 120 may not update data in place, SSD 120 may need to invalidate the existing data and write the update to a new PBA on SSD 120. Or, if the data is stored in a block that is selected for garbage collection, the data may be written to a new block on SSD 120 before the block is erased. By updating translation layer 325, machine 105 of FIG. 1 does not need to concern itself with where the data is actually stored as data is moved to different PBAs.

SSD 120 may also include processor 330, which may execute instructions that govern how to use SSD 120. Processor 330 may also be used for in-storage compute functionality, to execute operations locally on SSD 120 instead of on processor 110 of FIG. 1.

Finally, SSD 120 may include field programmable gate array (FPGA) 335. FPGA 335 may be used to implement added functionality within SSD 120, such as the DNA sequence analysis described below.

While FIG. 3 shows SSD 120 as including eight flash memory chips 315-1 through 315-8 organized into four channels 320-1 through 320-4, embodiments of the inventive concept may support any number of flash memory chips organized into any number of channels. Similarly, while FIG. 3 shows SSD controller 310 as including processor 330 and FPGA 335, embodiments of the inventive concept may place these elements in other locations. For example, FPGA 335 might be placed before host interface layer 305, outside SSD controller 310, or even outside SSD 120. For more discussion regarding the relative location of FPGA 335 and SSD 120, refer to co-pending U.S. patent application Ser. No. 16/435,442, filed Jun. 7, 2019, and its parent applications U.S. patent application Ser. No. 16/260,087, filed Jan. 28, 2019, U.S. patent application Ser. No. 16/226,629, filed Dec. 19, 2018, U.S. patent application Ser. No. 16/207,080, filed Nov. 30, 2018, U.S. Provisional Patent Application Ser. No. 62/745,261, filed Oct. 12, 2018, U.S. Provisional Patent Application Ser. No. 62/818,096, filed Mar. 13, 2019, and U.S. Provisional Patent Application Ser. No. 62/733,077, filed Sep. 18, 2018, all of which are incorporated by reference herein for all purposes.

Figure 4:
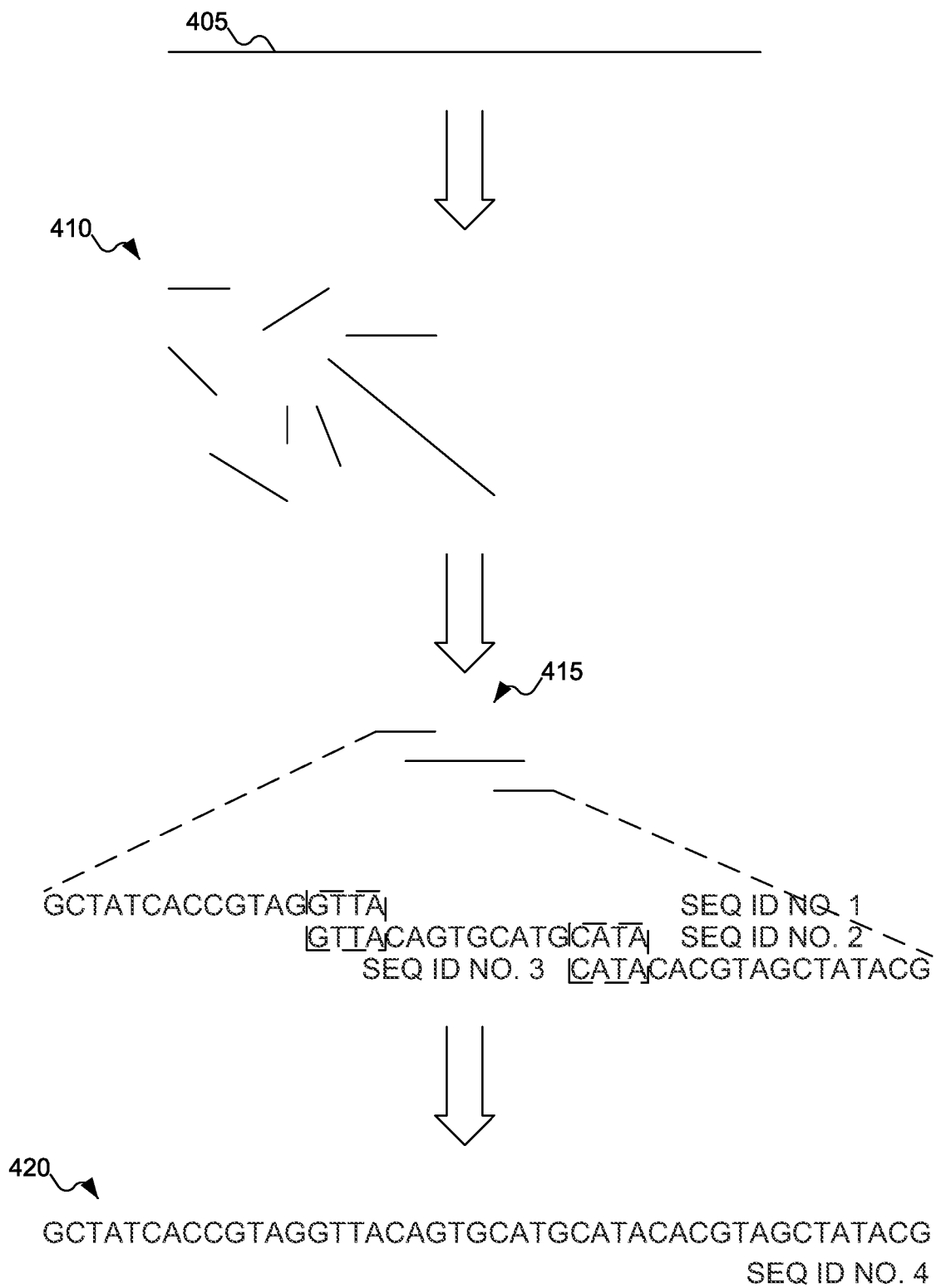
FIG. 4 shows an example process of breaking a DNA sequence into segments for analysis and reassembly, showing SEQ ID NO:1, SEQ ID NO:2, and SEQ ID NO:3 being assembled into SEQ ID NO:4.

FIG. 4 shows the process of breaking a DNA sequence into segments for analysis and reassembly. As shown in FIG. 4, DNA strand 405 may be very long: potentially hundreds of millions or more of nucleotides. Using known processes, DNA strand 405 may be broken down into short segments 410, typically including 30-100 nucleotides. Once broken, these short segments may be analyzed to determine the specific nucleotide sequence in each segment. But these short sequences may be also unordered: DNA sequence analysis may be performed to determine the relative order. For example, as shown trio of segments 415 may be relatively ordered by identifying portions that overlap, leading to the reconstructed DNA sequence shown as sequence 420.

Figures 5, 6:
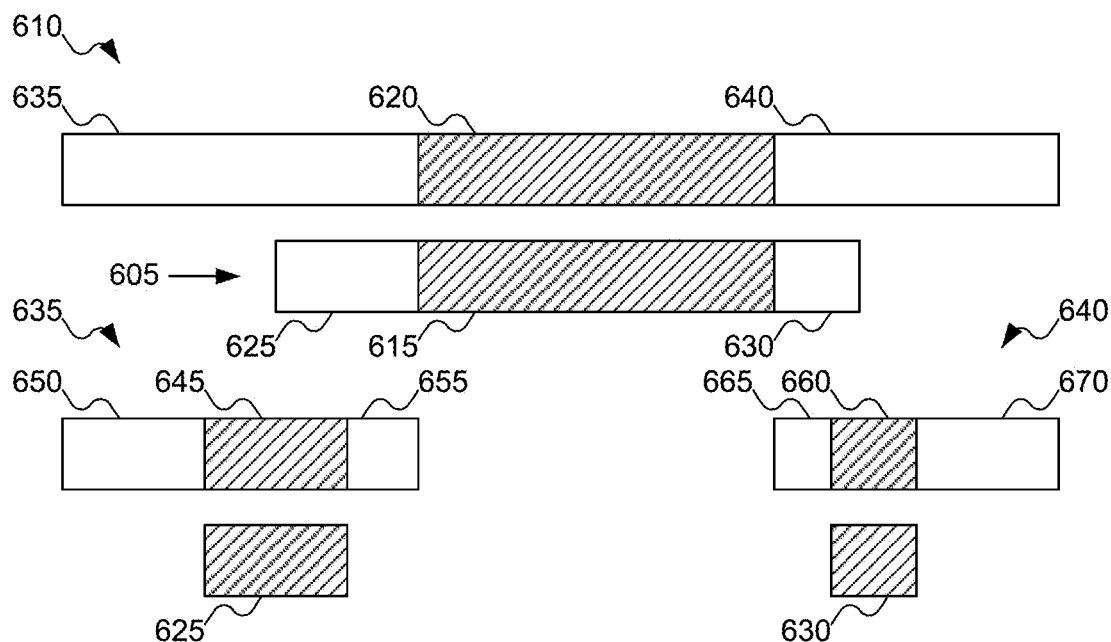
FIG. 5 illustrates some possible errors in SEQ ID NO:5, SEQ ID NO:6, and SEQ ID NO:7 during DNA sequence analysis.
FIG. 6 shows an example process of recursively performing DNA sequence analysis according to an embodiment of the inventive concept.

The process of generating short segments 410 may involve copying portions of DNA strand 405. This copying process may introduce errors. FIG. 5 illustrates common errors in DNA sequence analysis.

As shown in error 505, sometimes when a nucleotide is copied, it is copied incorrectly. For example, two nucleotide sequences are shown with a change in one nucleotide in the sequence. When a nucleotide is changed in this manner, the error may be referred to as a "single nucleotide polymorphism" (SNP).

On the other hand, as shown in error 510, sometimes the copying process inserts or deletes a nucleotide. For example, nucleotide sequence 2 includes a nucleotide missing from nucleotide sequence 1. Such errors may be referred to as "indels". (Whether the copying process inserts or deletes a nucleotide depends on which nucleotide sequence is considered the source and which is considered the copy: but either way, one nucleotide sequence includes a nucleotide missing from the other nucleotide sequence.)

FIG. 6 shows the process of recursively performing DNA sequence analysis according to an embodiment of the inventive concept. In FIG. 6, search sequence 605 may be compared with reference sequence 610. As part of this comparison, a continuous match of nucleotides may be found (shown as center portion 615 of search sequence 605 and center portion 620 of reference sequence 610, which are hashed): in some embodiments of the inventive concept, this continuous match of nucleotides may be the longest continuous match of nucleotides, whereas in other embodiments of the inventive concept this continuous match might not be the longest such continuous match of nucleotides. How the longest continuous match of nucleotides may be determined is discussed below with reference to FIGS. 9A-10. Once center portions 615 and 620 have been located, search sequence 605 may be divided into left portion 625, center portion 615, and right portion 630, and reference sequence 610 may be divided into left portion 635, center portion 620, and right portion 640. (Of course, this assumes that there are nucleotides to the left and right of center portions 615 and 620. If there are no nucleotides to one side or the other of a center portion, then the division may not produce either a left or right portion, or both.)

Once the left and right portions of search sequence 605 and reference sequence 610 have been located, the algorithm may be recursively performed on the relative portions. That is, left portion 625 may be searched relative to left portion 635, and right portion 630 may be searched relative to right portion 640. The recursion may end when no left portion and no right portion exist in at least one of search sequence 605 and reference sequence 610. Thus, as shown at the bottom of FIG. 6, left portion 625 may be searched relative to left portion 635, and may be matched (potentially recursively) as portion 645 of left portion 635. Similarly, right portion 630 may be searched relative to right portion 640, and may be matched (potentially recursively) as portion 660 of right portion 640. Note that the matching of left portion 625 against left portion 635 may leave unmatched parts of left portion 635 (such as portions 650 and 655). Similarly, the matching of right portion 630 against right portion 640 may leave unmatched parts of right portion 640 (such as portions 665 and 670). Unmatched parts 655 and 665 may be thought of as "gaps" between left portion 625, center portion 615, and right portion 630.

While FIG. 6 describes the above process as recursive, in the sense that the same analysis may be repeated on the left and right portions of search sequence 605 and reference sequence 610, recursion is not a requirement. That is, the above described process may be performed to find center portions 615 and 620, after which a different process may be used to analyze left portion 625 relative to left portion 635, and right portion 630 relative to right portion 640. But if the above process is performed again on the left and right portions of search sequence 605 and reference sequence 610, then the process may be said to be "recursive", whether or not that term is used.

Figure 7:
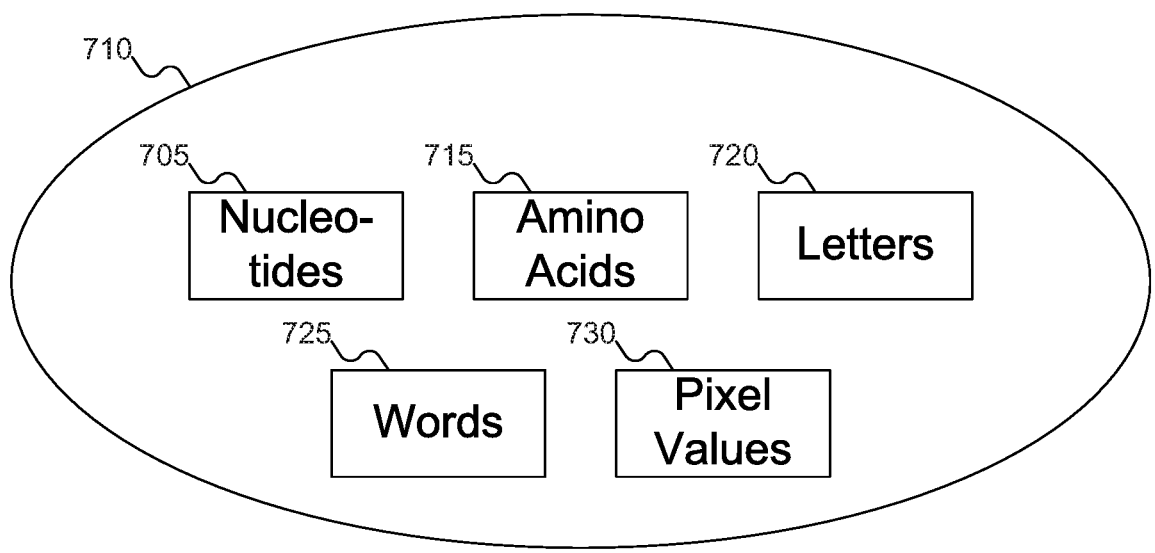
FIG. 7 shows examples of different atoms that may be used in embodiments of the inventive concept.

While the above discussion focuses on nucleotides in DNA sequencing, embodiments of the inventive concept may be used with other elements, termed "atoms". FIG. 7 shows examples of different atoms that may be used in embodiments of the inventive concept. Aside from nucleotides 705, atoms 710 may include, for example, amino acids 715, letters 720, words 725, and/or pixel values 730. Nucleotides include an alphabet of only four letters (Adenine Cytosine, Guanine, and Thymine which may be abbreviated A, C, G, and T), and exact matches may be required for DNA sequencing. In contrast, with other atoms, some variability may be permitted, and the degree of variability may vary depending on the atom in question. For example, there are 20 different amino acids that may occur in protein sequences. But two amino acids might be chemically similar even if molecularly different. Thus, two amino acid sequences might be considered effectively the same even with different literal sequences.

With letters 720, a search might consider the possibility of typographical errors. The word "firce", for example, is not a valid word. But it might be considered a typographical error based on "i" being typed instead of "o", or by omitting the letter "e" after "i". It may also be possible that "a" should have been typed instead of "o", but this may be less likely given the relative distance on a keyboard from "o" to "i" and "a". (Note that this distance measurement depends on the keyboard used: "a" is much farther from "o" than "i" on a QWERTY keyboard, but the same may not necessarily be true on alternative keyboard layouts.) Thus, a search of text that includes the word "force" or "fierce" might be considered a match, even though the search string included "firce".

When the atom is words 725, an approach similar to either amino acids 715 and/or letters 720 may be used. That is, minor variations might be considered to be equivalent words based on typographical distance on a keyboard, or by considering words that are similar in intent if different in spelling.

When the atom is pixels 730, the intensity, hue, or some other value (or combination of values) of the pixel may be used as the search value. When comparing a pixel in the search sequence with a pixel in the reference sequence, the distance between the two pixels may be measured based on the selected value(s). The "closer" the pixel in the search sequence may be to the pixel in the reference sequence, the more likely the pixels "match" for purposes of sequencing analysis. Using such information, it may be possible to determine whether two images may be considered similar based on a comparison of pixel-level information, even without an exact match.

As may be seen from these other choices for atoms, the comparison might not necessarily produce a binary result ("match" or "no match"), but instead include a range of possible results, similar to how fuzzy logic considers logical values other than just "true" and "false". In some embodiments of the inventive concept these values may range from 0 (representing "no match") to any positive value, up to and including infinity (representing "match"). In other embodiments of the inventive concept these values may be scaled between 0 and 1. In yet other embodiments of the inventive concept, these values may vary between any desired lower and upper bounds, either positive or negative.

Figure 8:
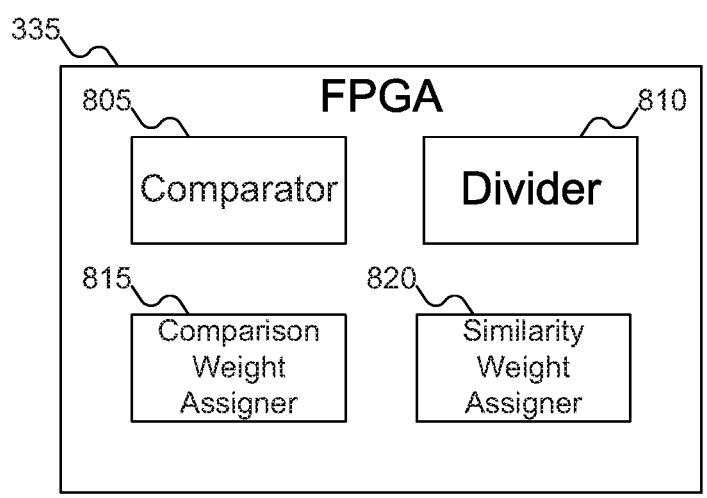
FIG. 8 shows some additional details of the field programmable gate array (FPGA) of FIG. 3.

FIG. 8 shows details of field programmable gate array (FPGA) 335 of FIG. 3. In FIG. 8, FPGA 335 is shown as including comparator 805, divider 810, comparison weight assigner 815, and similarity weight assigner 820. Comparator 805 may be used to compare a subsequence of search sequence 605 of FIG. 6 against reference sequence 610 of FIG. 6 to determine if the subsequence matches the reference sequence. Divider 810 may then divide search sequence 605 and reference sequence 610 into left portions 625 and 635 of FIG. 6, center portions 615 and 620 of FIG. 6, and right portions 630 and 640 of FIG. 6, so that the corresponding portions left and right portions may be recursively searched as well.

Comparison weight assigner 815 may assign weights to individual comparisons. As discussed further below with reference to FIGS. 9A-9B, different comparisons may be weighted to favor finding matches in particular locations within reference sequence 610 of FIG. 6, which may avoid biasing the sequence analysis. Comparison weight assigner 815 may assign weights using any desired scale: for example, weights may be assigned integer values or non-integer values, and the lower and upper bounds of the weights may be without any prior defined limits. Comparator 805 may use information from comparison weight assigner 815 in identifying the longest continuous match. Comparison weight assigner 815 is optional, and may be omitted.

Similarity weight assigner 820 may assign weights to various comparisons based on similarities. For example, as discussed above, the word "firce" might match against any of "force", "fierce", or "farce": but each possible match may have different levels of likelihood. In a similar manner also discussed above, different amino acids may have similar functionality even though they may be different in molecular structure. Similarity weight assigner 820 may assign the weights to a particular possible match based on how similar the atoms may be between search sequence 605 of FIG. 6 and reference sequence 610 of FIG. 6. Similarity weight assigner 820 may assign weights using any desired scale: for example, weights may be assigned integer values or non-integer values, and the lower and upper bounds of the weights may be without any prior defined limits. Comparator 805 may use information from similarity weight assigner 820 in identifying the longest continuous match. Like comparison weight assigner 815, similarity weight assigner 820 is optional, and may be omitted.

While FIG. 8 shows FPGA 335 as including various block elements, these elements should not necessarily be considered discrete elements. That is, embodiments of the inventive concept may or may not have circuits or equivalent structures that may be identified as performing the functions attributed to the various elements above. For example, FPGA 335 may instead be considered a single circuit that performs all of the functions described above, without individual circuit elements being identified as performing the individual functions separately.

Figure 9A:
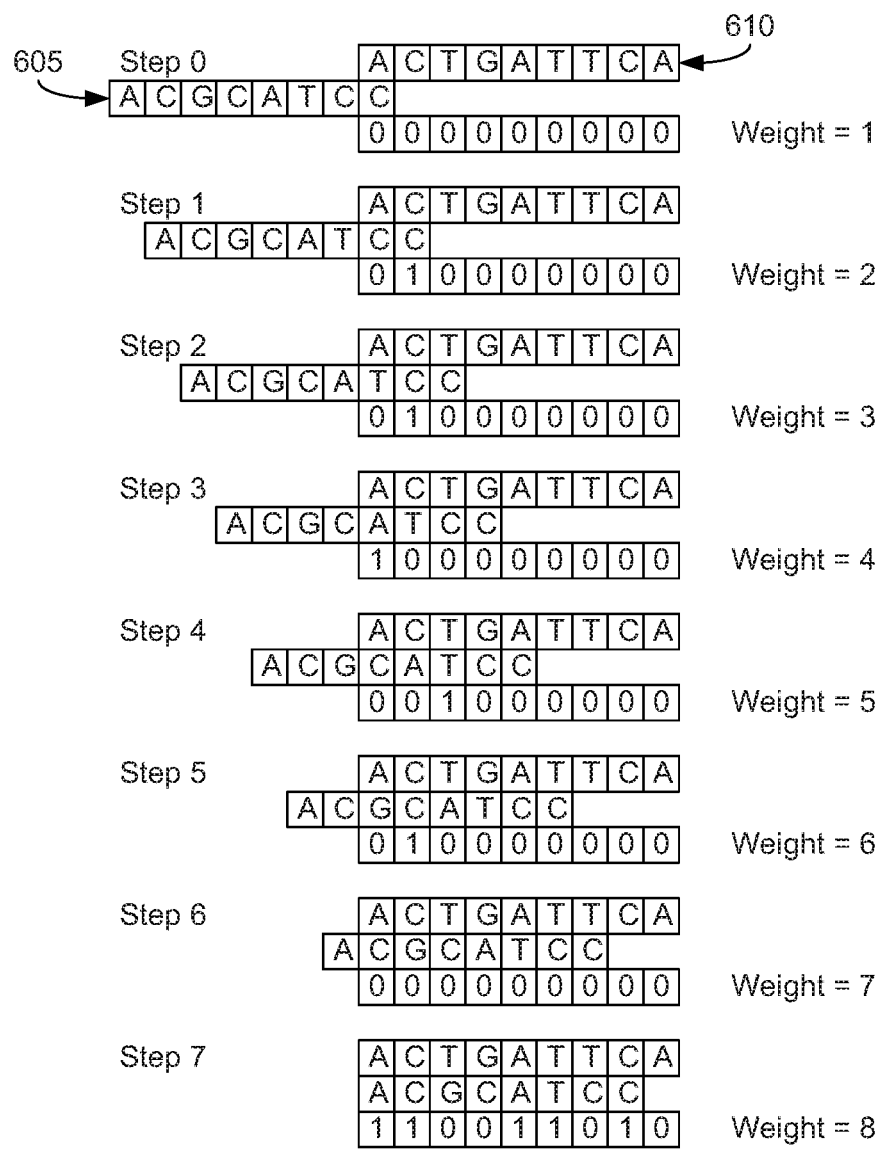

As discussed above, comparator 805 may identify the longest continuous match of atoms. FIGS. 9A-9B illustrate how this can be done, along with the possible consideration of weights used in selecting the best match.

In FIGS. 9A-9B, search sequence 605 may be compared with reference sequence 610 over a number of steps. At each step, a subsequence of search sequence 605 may be compared with a subsequence of reference sequence 610, with at least one of each subsequence being different relative to any other step. Thus, for example, in step 0 subsequence "C" of search sequence 605 may be compared against subsequence "A" of reference sequence 610, in step 1 subsequence "CC" may be compared against subsequence "AC" of reference sequence 605, and so on. (Ignore for the moment the weights assigned to each step.) At each step the comparison of individual atoms may represented as a sequence of is and 0s, with "1" indicating a match" and "0" indicating no match. The subsequence of search sequence 605 that includes the highest number of matched atoms with the subsequence of reference sequence 610—found in step 7—may be selected as the best match.

Figure 10:
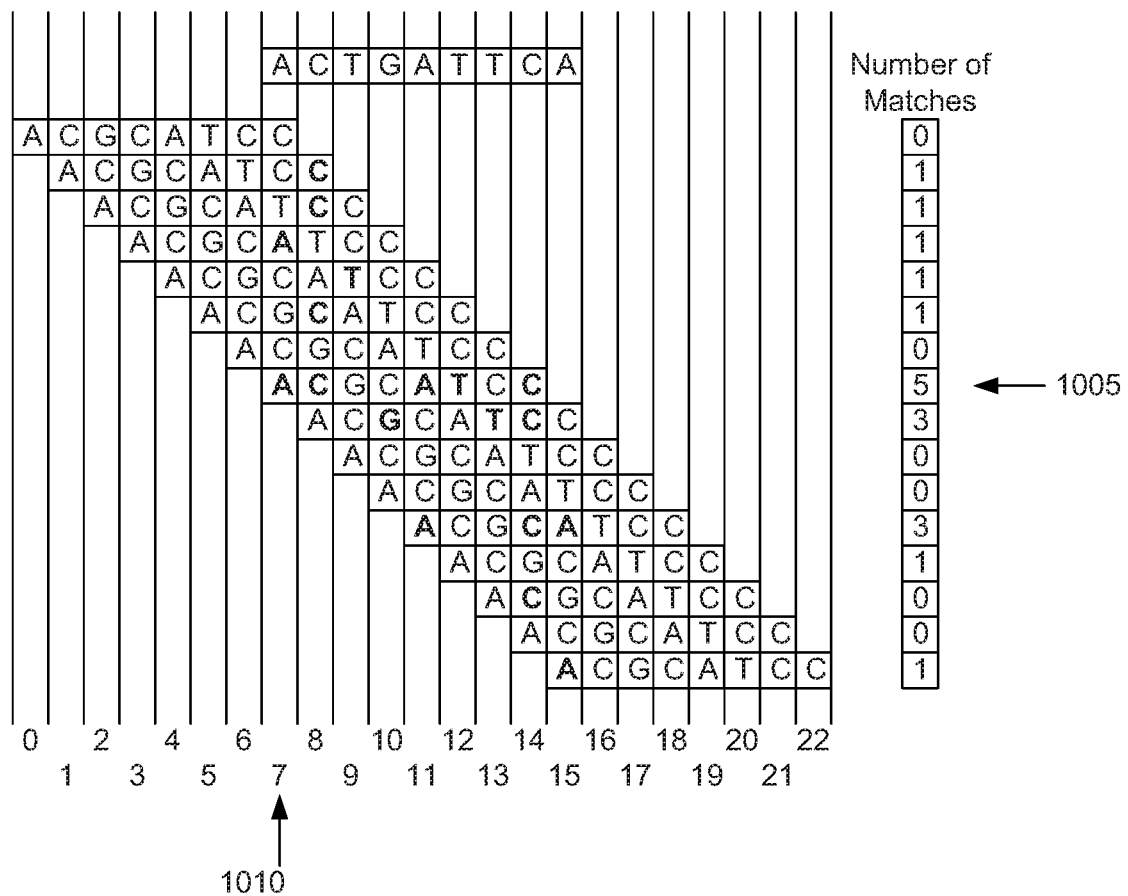
FIG. 10 shows an example operation of identifying a longest continuous match between a search sequence and a reference sequence.

FIG. 10 illustrates this in a manner showing the total number of matches for each comparison in FIGS. 9A-9B. Note that the comparison that has the largest total number of matches does not necessarily mean that the sequence of matches is continuous. For example, in row 1005, at step 1010, there are a total of three separate sequences that match: "AC", "AT", and "C". Instead of counting the total number of matches in the comparison, the sequence analysis might count the number of atoms in the longest continuous match in the comparison, in which case the number of matches would be "2", not "5". (But also note that in the analysis shown, the same step might be chosen for the longest continuous match since no step has a continuous match that is longer than two atoms, and the total number of matches, as an alternative to (or in addition to) weights, may be used as a "tie breaker" when multiple steps include the same number of atoms in the longest continuous match.) Since row 1005 includes the highest number of matches (as well as tying for the longest continuous match), step 7 may be selected as the comparison including the longest continuous match of atoms.

Having identified the step that includes the highest number of matches, the sequence analysis may now identify the longest continuous match of atoms. In a step where there may be only one longest continuous match of atoms, the longest continuous match of atoms may be selected. But in this example, as there are two different sequences each including two consecutive atoms, the comparison may select either sequence as the longest continuous match of atoms, either arbitrarily or based on some criteria, such as which sequence may be closest to a preferred point of matching in the reference sequence. For example, using a preference for center matching the sequence "AT" may be selected as the longest continuous match of atoms, whereas using a preference for left matching the sequence "AC" may be selected as the longest continuous match of atoms.

Once comparator 805 of FIG. 8 has identified the longest continuous match of atoms, divider 810 of FIG. 8 may now divide search sequence 605 of FIG. 6 and reference sequence 610 of FIG. 6 into left, center, and right portions. Center portions 615 and 620 of FIG. 6 may be selected as including the longest continuous match of atoms, whereas left portions 625 and 635 of FIG. 6 may include the atoms to the left of the longest continuous match of atoms and right portions 630 and 640 of FIG. 6 may include the atoms to the right of the longest continuous match of atoms. Thus, if the longest continuous match of atoms may be selected as "AT", then left portion 625 of FIG. 6 includes "ACGC", left portion 635 of FIG. 6 includes "ACTG", right portion 630 of FIG. 6 includes "CC", and right portion 640 of FIG. 6 includes "TCA". On the other hand, if the longest continuous match of atoms may be selected as "AC", then left portion 625 of FIG. 6 is blank, left portion 635 of FIG. 6 is blank, right portion 630 of FIG. 6 includes "GCATCC", and right portion 640 of FIG. 6 includes "TGATTCA". FPGA 335 of FIG. 3 may then recursively perform an analysis using left portions 625 and 635 of FIG. 6 and right portions 630 and 640 of FIG. 6. (If the longest continuous match may be selected as "AC", then left portions 625 and 635 of FIG. 6 are blank, so no search for a match of left portions 625 and 635 of FIG. 6 may need to be performed.)

Returning to FIGS. 9A-9B, the weights are now explained. In FIGS. 9A-9B a preference for center matching is shown. Thus, comparison weight assigner 815 of FIG. 8 may assign the highest weights to the matches closest to the center of search sequence 605 and reference sequence 610, with the weights becoming progressively smaller further from the center. Thus, a weight of 1 may be assigned to steps 0 and 15, a weight of 2 may be assigned to steps 1 and 14, and so on.

If the preference is for left matching, then comparison weight assigner 815 of FIG. 8 may assign the highest weight where the entirety of search sequence 605 of FIG. 6 matches at the start of reference sequence 610 of FIG. 6: at step 7 in FIGS. 9A-9B, with decreasing weights left and right from that point. Similarly, if the preference would be for right matching, then comparison weight assigner 815 of FIG. 8 may assign the highest weight where the entirety of search sequence 605 of FIG. 6 matches at the end of reference sequence 610 of FIG. 6: at step 8 in FIGS. 9A-9B, with decreasing weights left and right from that point. (Since having both positive and negative weights may result in some possible matches being completely excluded, the weights may be assigned so that all weights may be either positive or negative, as desired. Of course, if discouraging selection of matches too far from the target point is desired, then it may be possible to mix positive and negative weights.)

While the above discussion focuses on comparison weight assigner 815 of FIG. 8, a similar approach may be used with similarity weight assigner 820 of FIG. 8, except that the weights then depend on how similar the subsequences are rather than their relative position. Comparator 805 of FIG. 8 may use similarity weight assigner 820 of FIG. 8 to assign higher weights to matches that may be more similar, and lower weights to matches that may be less similar.

But using similarity weight assigner 820 of FIG. 8 introduces a wrinkle not present when using comparison weight assigner 815 of FIG. 8: specifically, how to determine where an alignment ends. When matches are binary in nature—either two atoms match or two atoms differ—it is easy to determine where a match sequence begins and ends. For example, in step 7 (shown in FIG. 9A), there are three match sequences: "AC" (the first two atoms in the sequences), "AT" (the fifth and sixth atoms in the sequences), and "C" (the eight atom in the sequences). Any atoms that do not match may not be part of the match sequence.

But where matches are not binary but may take on a range of values (as may occur when using similarly weight assigner 820 of FIG. 8), it becomes more difficult to tell where a match sequence begins and ends. With non-binary matches, it is rare that the result of a comparison of atoms returns a true 0 (no match) value. Instead, the value returned may be non-zero, with the value indicating a relative likelihood of match. For example, a comparison of "i" with "o" may result in a value that is lower than an exact match but higher than a comparison of "a" with "o", because "i" is much closer to "o" on the standard QWERTY keyboard than "a"). Without a definitive "no match" value being returned, it may be more difficult to identify where a match sequence begins and ends.

The solution to this problem is to set a threshold value (also called a cut-off value), and to decide that a particular comparison of atoms is considered not to be a match if the result of its comparison is less than the threshold value. For example, if the result of comparisons is scaled between 0 and 1 (with "0" meaning no match and "1" meaning an exact match), a threshold value of 0.1 may be used. Any comparison of atoms that returns a result below this threshold may be said to be considered no match, and therefore may represent outside a match sequence. Conversely, any comparison of atoms that returns a result equal to or greater than this threshold may be said to be considered a match and there part of a match sequence. Once the ends of a particular match sequence have been identified, embodiments of the inventive concept may proceed to identify the left and right portions of the sequences that are not considered part of the match sequence, as described above with reference to FIG. 6.

The threshold value may be set by a user of the system, or it may be determined based on information in matrices that store information about the relative similarity of atoms. For example, when amino acids are used as atoms, a BLOSUM or PAM matrix may be used to provide relative similarity information regarding the amino acids, and the threshold value may be derived from these matrices. Similarly, when letters are used as atoms, a matrix may represent the likelihood that any one particular character was mistyped as any other particular character. The threshold value may be derived in any desired manner: for example, by ranking the values in the matrix and selecting a value at a particular entry (such as the fifth entry from the bottom, or at a percentage of the total number of values). Similarly, while the above discussion describes the results of comparisons as ranging from 0 to 1, and other range limits may be used, without limitation.

In all of the above discussion, the terms "higher weight" and "lower weight" are relative to the implementation. For example, if the algorithm relies on positive weighting, then a "higher weight" would use a number that is numerically larger than a "lower weight". On the other hand, if the algorithm uses negative weighting, then a "higher weight" may use a number that is numerically smaller than a "lower weight". The terms "higher" and "lower" should not be interpreted as necessarily implying a specific numerical relationship.

Once weights are assigned to each comparison, the weights may be multiplied by the number of matches (or the length of the longest continuous match), step for step. Thus, for example, step 1 (FIG. 9A) has a weight of 2 and one atom matched, for a total value of 2; step 7, on the other hand, has a weight of 8 and 5 atoms matched, for a total value of 40 (or 16, if using the length of the longest continuous match). In embodiments of the inventive concept where weights are used, the highest value (factoring in both the weight and either the number of matches or the length of the longest continuous match) may be used to select the step considered to have the desired longest continuous match, after which the sequence analysis proceeds as above.

In embodiments of the inventive concept where weights are used, it may be possible that the weight applied at a particular step may become more of a factor than the number of matches (or the length of the longest continuous match). For example, if a step with a weight of 4 has a total of 8 matched atoms (for a total value of 32) and another step with a weight of 5 has a total of 7 matched atoms (for a total value of 35), the latter step would be selected even though it has fewer total matched atoms. This situation may result in a local maximization that prevents the sequence analysis from finding the optimal solution. To help address this situation, more than one step may be selected for further analysis. Since the sequence analysis enables parallel analysis of multiple search sequences (rather than the linear analysis in conventional solutions), exploring alternative avenues of solution in this manner may not require any additional time over and above the time required to follow the avenue that produces the local maximum.

To select more than one step for parallel analysis, any suitable approach may be used. For example, all steps that may be within a particular "distance" from the selected step (such as all steps with a total value that is within some delta of the total value of the selected step, or within some percentage of the total value of the selected step) may be explored. Alternatively, rather than selecting the step with the highest total value, some predetermined number of steps (for example, three) with the highest total values overall may be explored. Embodiments of the inventive concept may also include other techniques to select additional steps for further parallel exploration.

In general, every possible subsequence of search sequence 605 may be compared against every possible subsequence of reference sequence 610. But while it may be sufficient to compare every possible subsequence of search sequence 605 against every possible subsequence of reference sequence 610, such may be not necessary. A review of FIGS. 9A-9B suggests various rules identifying which subsequences of search sequence 605 may be compared against which subsequences of reference sequence 610. These rules may include:

1) Any subsequence of search sequence 605 includes either the atom at the left end of search sequence 605 or the atom at the right end of search sequence 605, and possibly both such atoms ("left" and "right" being terms chosen to represent the start and end of search sequence 605: other terms may be used with equal understanding, such as "first" and "last", "top" and "bottom", and so on, with either term in any pair being applied to either end of search sequence 605).

2) If a subsequence of search sequence 605 is shorter than search sequence 605 (that is, search sequence 605 includes at least one atom not included in the subsequence), that subsequence may be compared with a subsequence of equal length from reference sequence 610 that includes the atom at the opposite end of reference sequence 605. Thus, for example, any subsequence that includes the "A" at the left end of search sequence 605 would be compared with a subsequence of reference sequence 610 that includes the "A" at the right end of reference sequence 610; and any subsequence that includes the "C" at the right end of search sequence 605 would be compared with a subsequence of reference sequence 610 that includes the "A" at the left end of reference sequence 610.

3) If the entirety of search sequence 605 is being compared with reference sequence 610, then search sequence 605 may be compared with every subsequence of reference sequence 610 of the same length as search sequence 605.

4) The above rules assume that search sequence 605 is no longer than reference sequence 610. If search sequence 605 is longer than reference sequence 605, the roles of search sequence 605 and reference sequence 610 may be reversed in the rules above.

Figure 11:
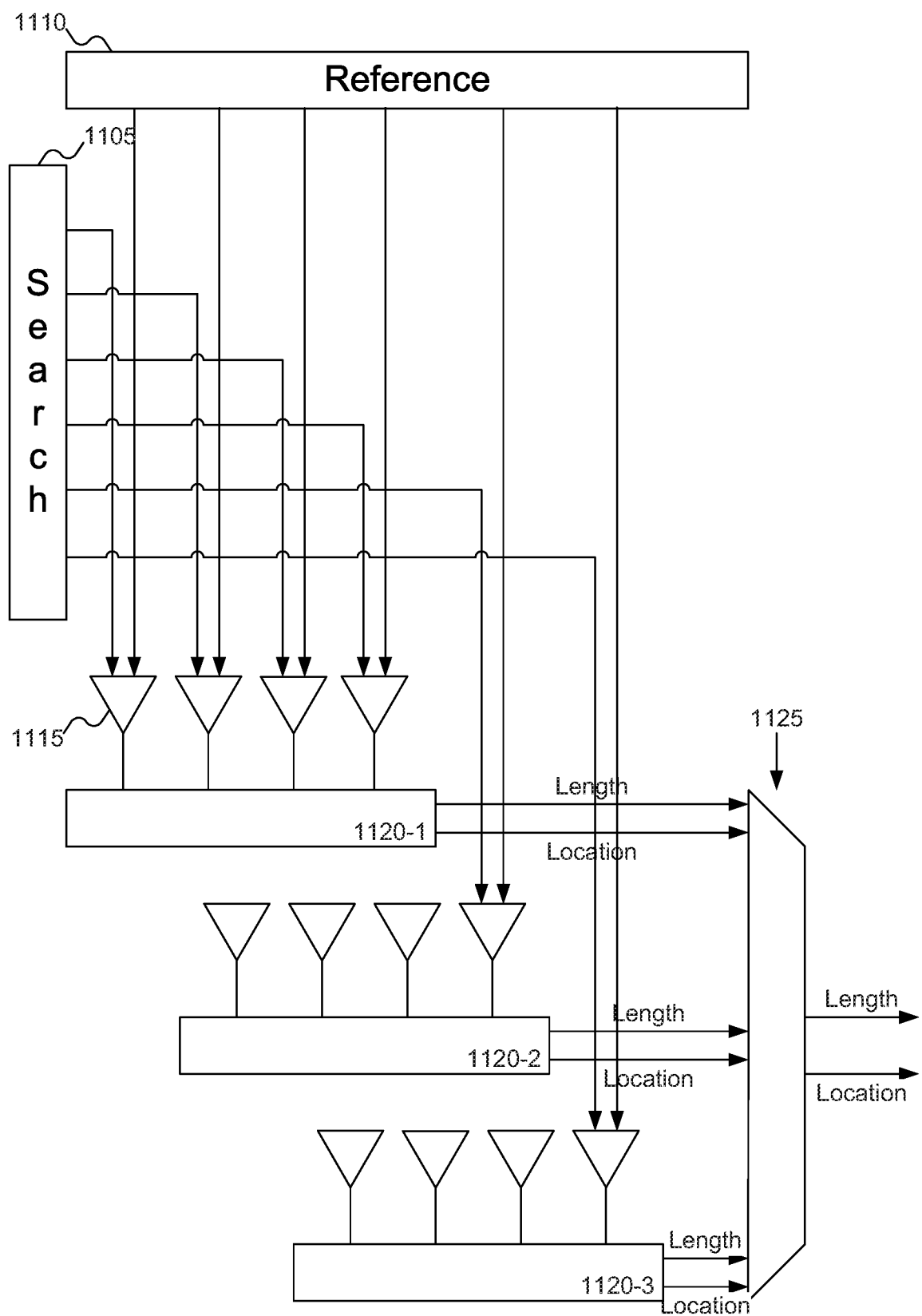
FIG. 11 shows a circuit structure that may identify a longest continuous match between a search subsequence and a reference subsequence.

FIG. 11 shows a circuit structure that may be configured to identify a longest continuous match between a search subsequence and a reference subsequence. In FIG. 11, given search subsequence 1105 and reference subsequence 1110, individual atoms may be input to individual atom comparators, such as atom comparator 1115, which input results to analyzers 1120-1, 1120-2, and 1120-3. Analyzers 1120-1, 1120-2, and 1120-3 may then identify the longest continuous match (or the total number of matches) based on the atoms input to atom comparators 1115, and may output this information to selector 1125, which may then return the longest continuous match (or the step that includes the highest number of matches) as well as the location of the longest continuous match.

A few notes about FIG. 11 are in order. First, FIG. 11 shows three analyzers 1120-1, 1120-2, and 1120-3. But there may be any number of analyzers: the total number may vary depending on the lengths of search subsequence 1105 and reference subsequence 1110.

Second, analyzers 1120-1, 1120-2, and 1120-3 are shown as receiving input from four atom comparators like atom comparator 1115 each. But the number of atom comparators providing input to analyzers 1120-1, 1120-2, and 1120-3 may vary, depending on the lengths of the subsequences being input. Further, if the circuit of FIG. 11 may be intended to compare subsequences of search sequence 605 of FIG. 6 of varying lengths with reference sequence 610 of FIG. 6, then the number of inputs to analyzers 1120-1, 1120-2, and 1120-3 may vary. For example, as shown in FIGS. 9A-9B, steps 0 and 15 each compare a single atom from search sequence 605 of FIG. 6 against a single atom of reference sequence 610 of FIG. 6, steps 1 and 14 each compare two atoms from search sequence 605 of FIG. 6 against two atoms of reference sequence 610 of FIG. 6, and so on (up to steps 7 and 8, which compare seven atoms—the length of search sequence 605 of FIG. 6—against reference sequence 610 of FIG. 6). Thus, the number of atom comparators providing input to each analyzer may vary based on the length of the subsequence being considered in the current step. Further, a single atom in each of search subsequence 1105 may be compared against multiple atoms in reference subsequence 1110, as the subsequence (or portions of it) may be "slid" relative to reference subsequence 1110.

Finally, as should be apparent from the prior discussion, while FIG. 11 shows search subsequence 1105 and reference subsequence 1110, the term "subsequence" could mean a continuous sequence of atoms from either search sequence 605 of FIG. 6 or reference sequence 610 of FIG. 6, or it could mean the entirety of search sequence 605 of FIG. 6 or reference sequence 610 of FIG. 6. In other words, the term "subsequence" is not intended to imply that it is necessarily shorter in length than the sequence from which is was obtained.

It is understood that a measure of the similarity between two functions, or two sequences in case of the discrete domain, may be given by the cross-correlation between the two functions or two sequences. Cross-correlation between two discrete sequences A[m] and B [m], where A and B may be two integer or real numbers, may be defined as a function C[n] obtained by sliding the two sequences one against the other by an amount n and adding together the products obtained by multiplying the corresponding elements of A[m] and B [m], similar to the circuit shown in FIG. 11. Thus, FIG. 12 shows a circuit structure to perform cross-correlation between a search subsequence and a reference subsequence.

Figure 12:
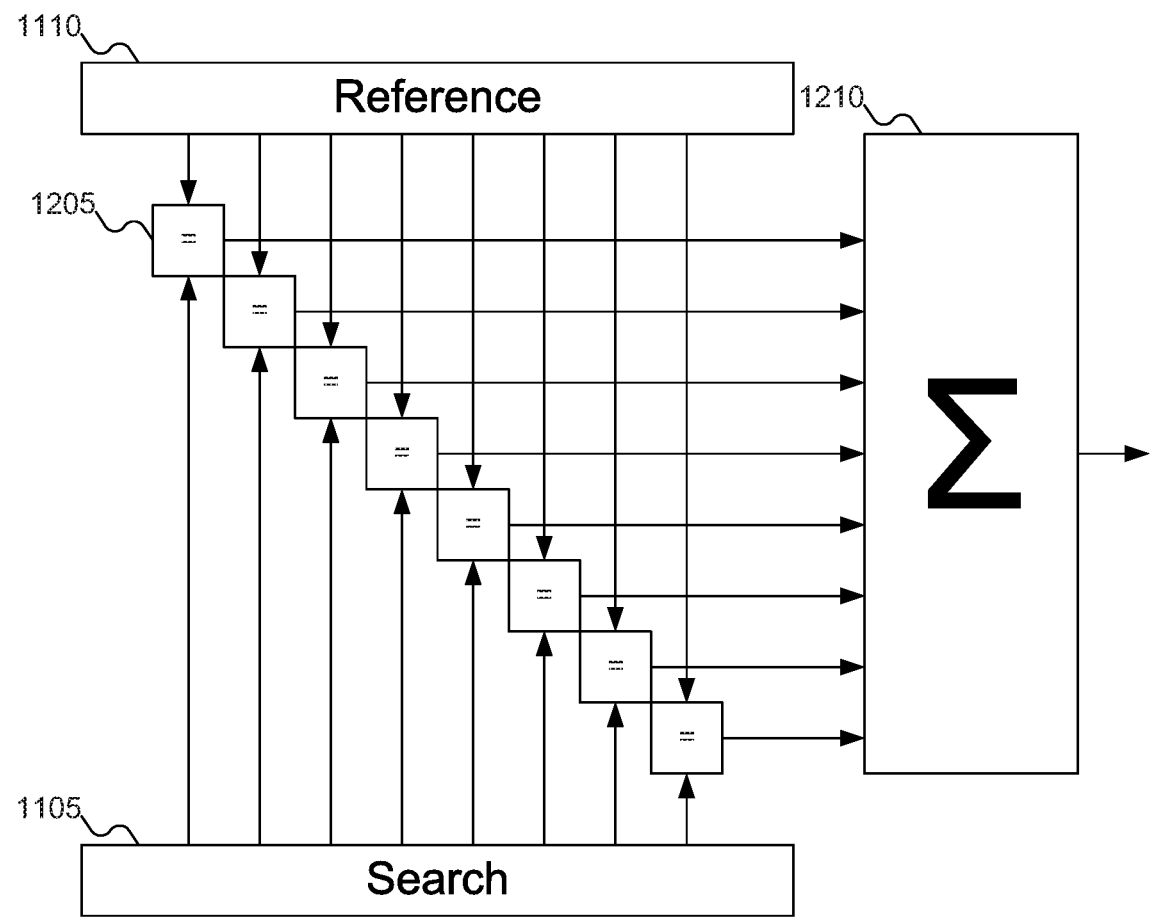
FIG. 12 shows a circuit structure that may perform a cross-correlation between a search sequence and a reference sequence.

In FIG. 12, given a particular pair of search subsequence 1105 and reference subsequence 1110, atom comparators 1205 may compare individual corresponding atoms in search subsequence 1105 and reference subsequence 1110. Atom comparators 1205 may return any desired result of the comparison of the two atoms: 0 and 1 may be used, as may any other desired value pairs. Sum operator 1210 may then sum the values produced by atom comparators 1205, producing an output that represents the cross-correlation between search sequence 1105 and reference sequence 1110. Note that the output of the circuit of FIG. 12 produces a value that may be considered a (potentially diluted) form of the output of analyzers 1120-1, 1120-2, and 1120-3 of FIG. 11, and thus may be used as a partial example of the implementation of analyzers 1120-1, 1120-2, and 1120-3 of FIG. 11 (the missing elements being the location of the longest continuous match of atoms found by each analyzer and the length of just the longest continuous match of atoms found by each analyzer (rather than all matches). The circuit of FIG. 12 may be used, for example, to determine the number of matches for any individual step, as shown in FIGS. 9A-9B.

Figure 13A:
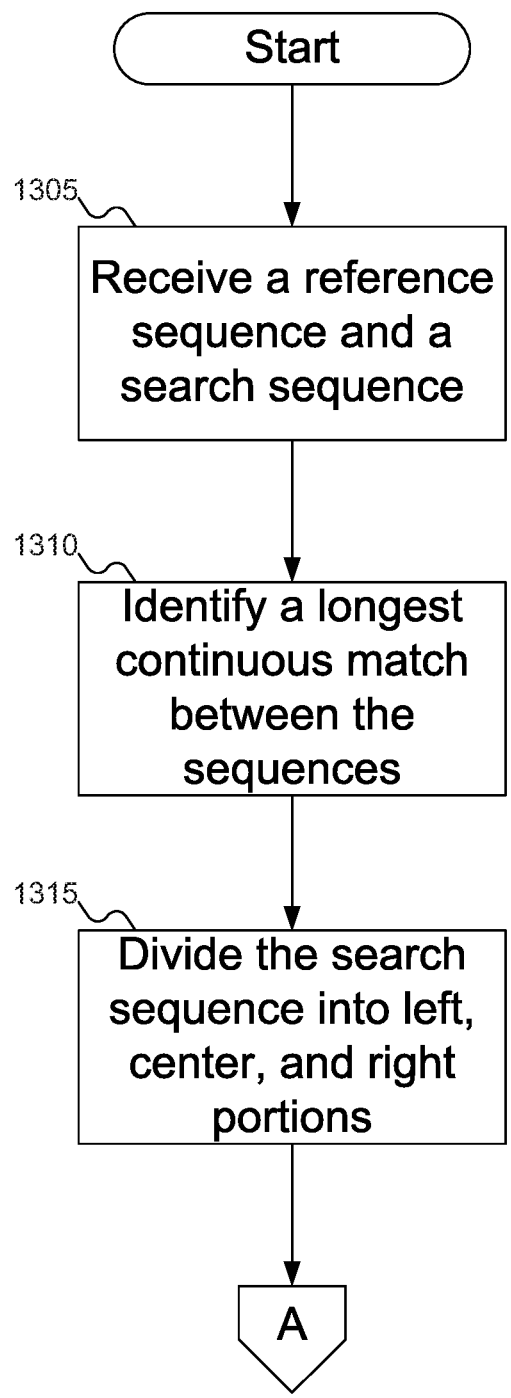
FIGS. 13A-13B show a flowchart of an example procedure to perform sequencing analysis, according to an embodiment of the inventive concept.
Figure 13B:
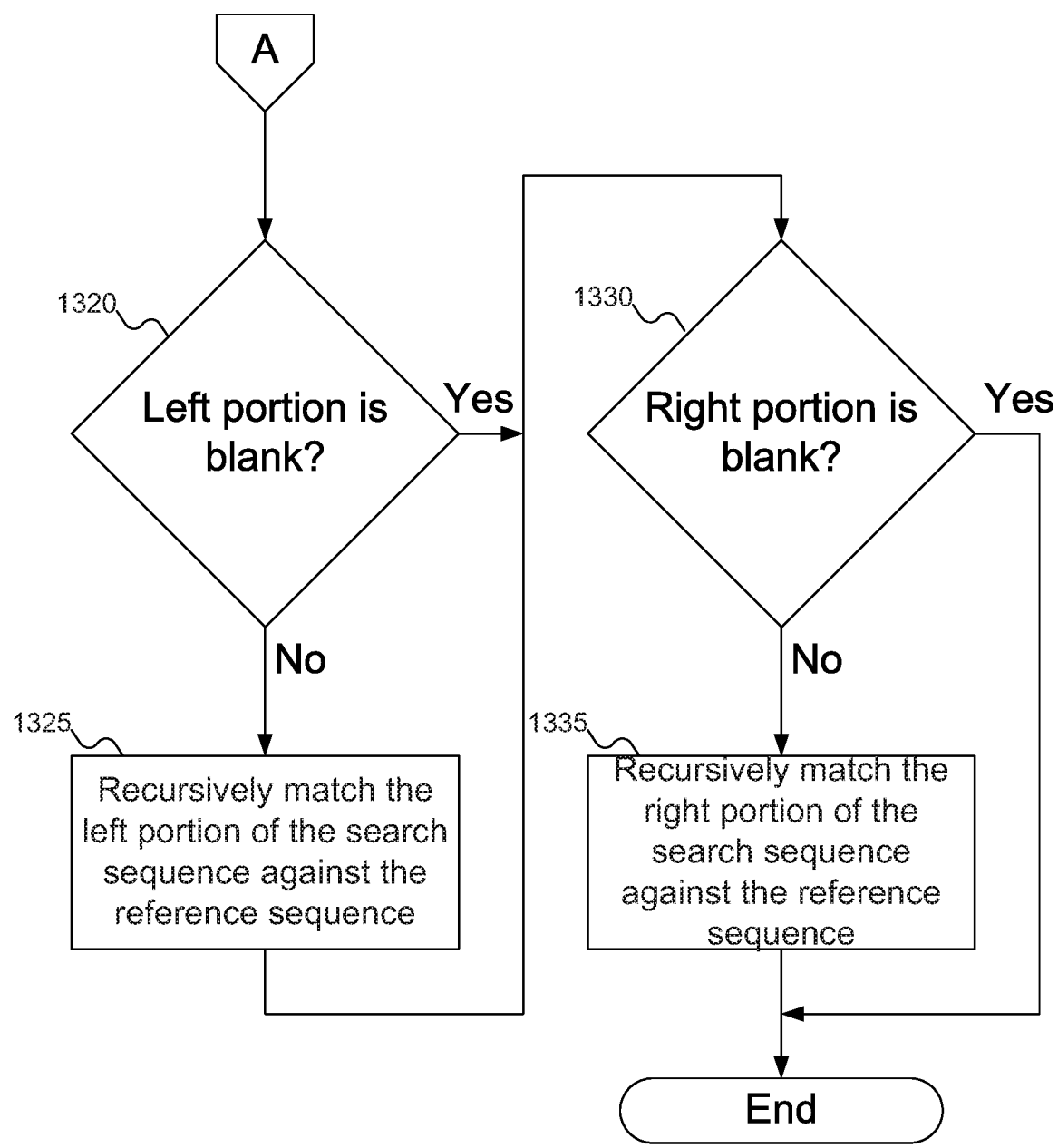

FIGS. 13A-13B show a flowchart of an example procedure to perform sequencing analysis according to an embodiment of the inventive concept. In FIG. 13A, at block 1305, comparator 805 of FIG. 8 may receive search sequence 605 of FIG. 6 and reference sequence 610 of FIG. 6. At block 1310, comparator 805 of FIG. 8 may identify the longest continuous match of atoms between search sequence 605 of FIG. 6 and reference sequence 610 of FIG. 6. At block 1315, divider 810 of FIG. 8 may divide search sequence 605 of FIG. 6 into left portion 625 of FIG. 6, center portion 615 of FIG. 6, and right portion 630 of FIG. 6. Divider 810 of FIG. 8 may also divide reference sequence 610 of FIG. 6 into left portion 635 of FIG. 6, center portion 620 of FIG. 6, and right portion 640 of FIG. 6.

At block 1320 (FIG. 13B), FPGA 335 of FIG. 3 may determine if left portion 625 of FIG. 6 is blank or includes at least one atom. If left portion 625 includes at least one atom, then at block 1325, FPGA 335 of FIG. 3 may recursively analyze left portion 625 of FIG. 6 and left portion 635 of FIG. 6. At block 1330, FPGA 335 of FIG. 3 may determine if right portion 630 of FIG. 6 is blank or includes at least one atom. If right portion 630 includes at least one atom, then at block 1335, FPGA 335 of FIG. 3 may recursively analyze right portion 630 of FIG. 6 and right portion 640 of FIG. 6.

Figure 14A:
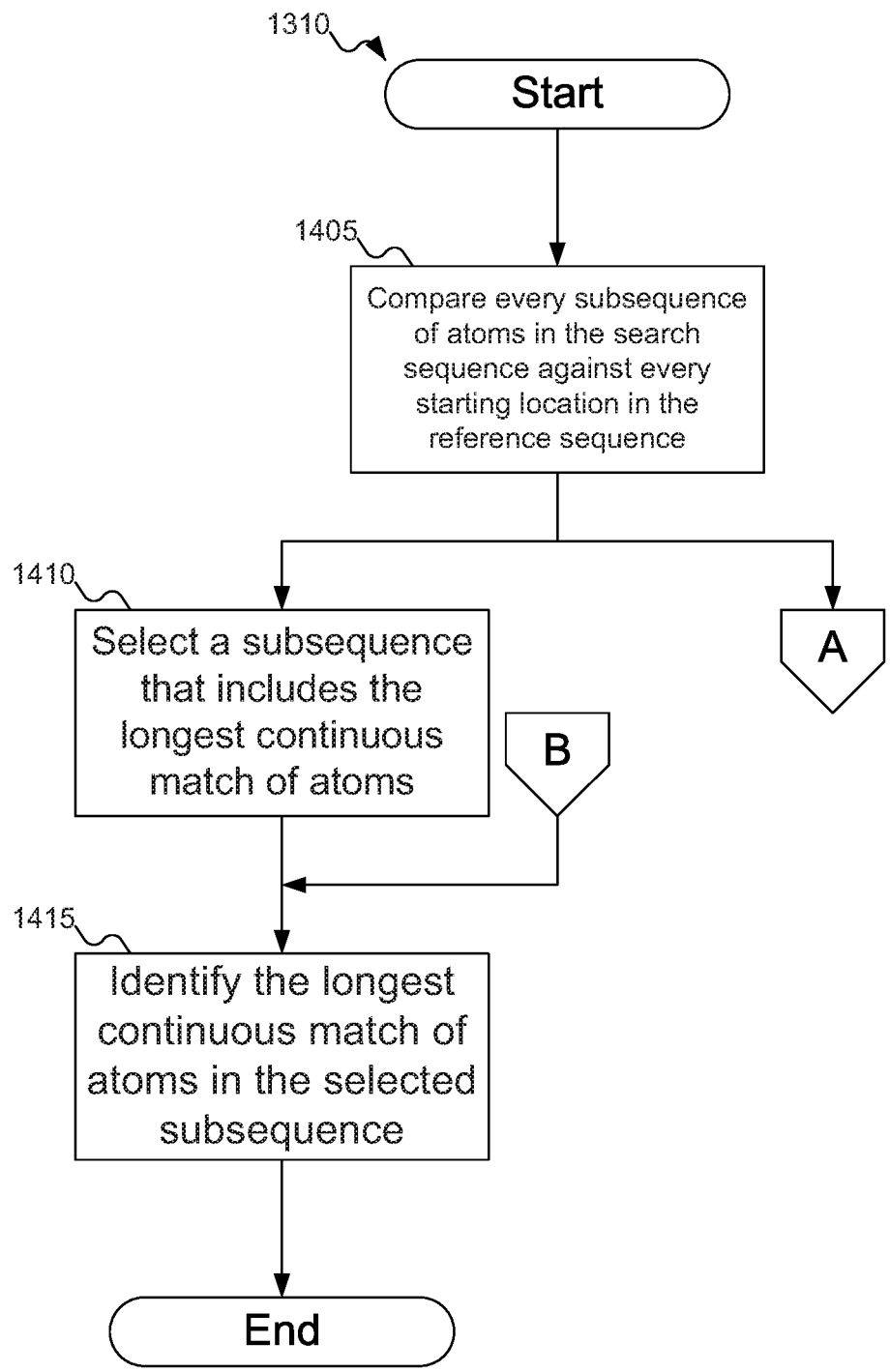
FIGS. 14A-14B show a flowchart of an example procedure to identify a match in the sequencing analysis of FIGS. 13A-13B, according to an embodiment of the inventive concept.
Figure 14B:
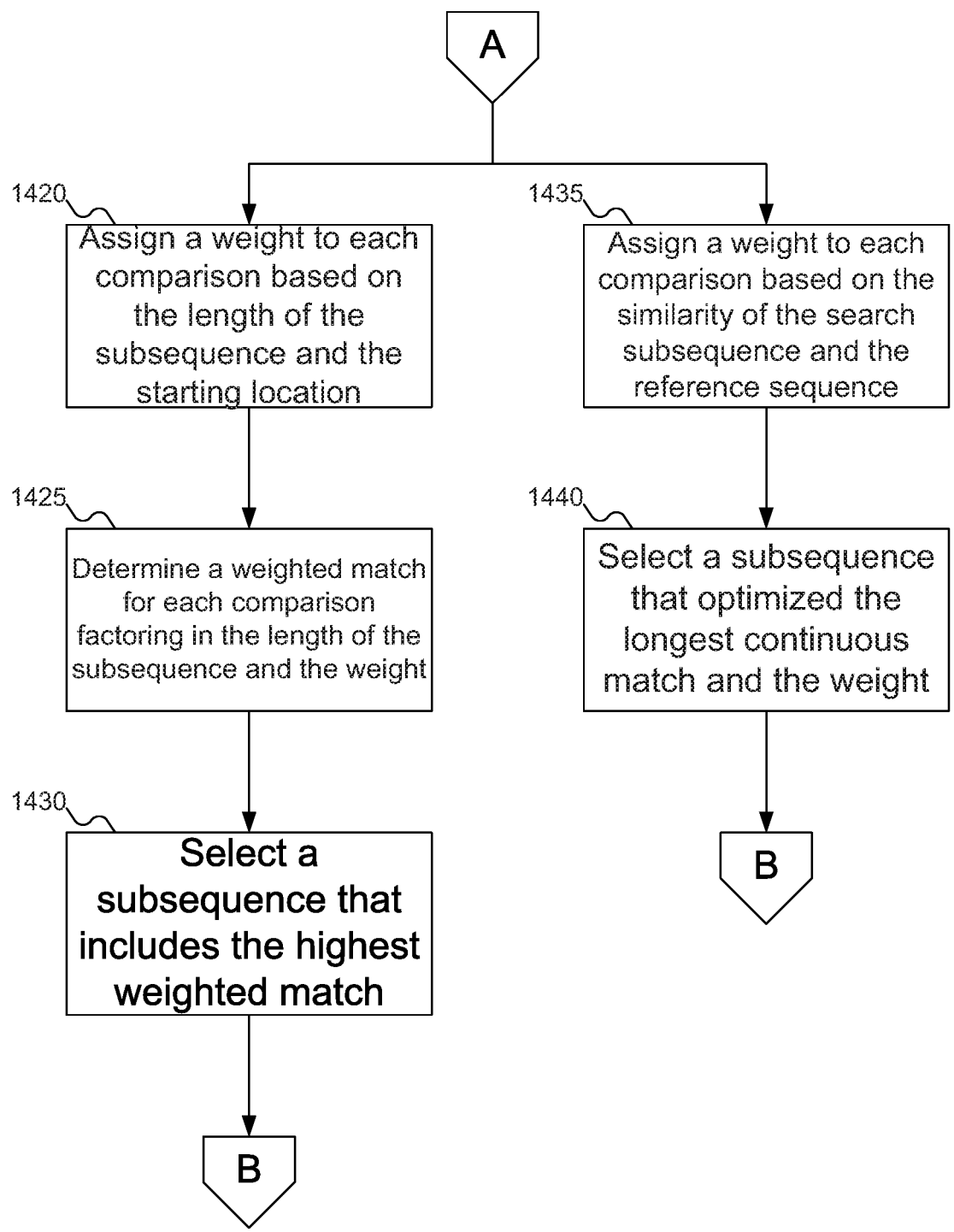

FIGS. 14A-14B show a flowchart of an example procedure to identify a match in the sequencing analysis of FIGS. 13A-13B, according to an embodiment of the inventive concept. In FIG. 14A, at block 1405, comparator 805 of FIG. 8 may compare every subsequence of search sequence 605 of FIG. 6 with every subsequence of reference sequence 610 of FIG. 6. (As discussed above, it may not be necessary to compare every subsequence search sequence 605 of FIG. 6 with every subsequence of reference sequence 610 of FIG. 6: a more selective comparison based on the rules provided above may be used.) At block 1410, comparator 805 of FIG. 8 may then select the subsequence that includes the longest continuous match of atoms, and at block 1415 comparator 805 of FIG. 8 may identify the longest continuous match of atoms in the selected subsequence as center portions 615 and 620 of FIG. 6.

Alternatively, instead of simply selecting the longest continuous match of atoms, at block 1420 (FIG. 14B), comparison weight assigner 815 of FIG. 8 may assign a weight to each comparison based on the length of the subsequences being compared and their location in reference sequence 610 of FIG. 6. Then, at block 1425, comparator 805 of FIG. 8 may determine a weighted match for each comparison, factoring in both the length of the longest continuous match of atoms in that comparison (or the total number of matches in that comparison) and the weight. This factoring may be performed by multiplying the two values together to produce the weighted match. Finally, at block 1430, comparator 805 of FIG. 8 may select the comparison with the highest weighted match, after which processing may return to block 1415 of FIG. 14A to identify the longest continuous match in that subsequence.

Alternatively, instead of simply selecting the longest continuous match of atoms, at block 1435 (FIG. 14B), similarity weight assigner 820 of FIG. 8 may assign a weight to each comparison based on the similarity of the subsequences being compared. Then, at block 1440, comparator 805 of FIG. 8 may select the comparison that optimizes both the longest continuous match of atoms and the weight. This optimization may be performed by multiplying the two values together to produce the weighted match. Finally, processing may return to block 1415 of FIG. 14A to identify the longest continuous match in that subsequence.

While FIG. 14B shows two different alternative approaches (in blocks 1420 through 1430 and in blocks 1435 through 1440), embodiments of the inventive concept may combine both approaches together. That is, comparator 805 of FIG. 8 may apply weights assigned by both comparison weight assigner 815 of FIG. 8 and similarity weight assigner 820 of FIG. 8.

In FIGS. 13A-14B, some embodiments of the inventive concept are shown. But a person skilled in the art will recognize that other embodiments of the inventive concept are also possible, by changing the order of the blocks, by omitting blocks, or by including links not shown in the drawings. All such variations of the flowcharts are considered to be embodiments of the inventive concept, whether expressly described or not.

Embodiments of the inventive concept offer technical advantages over the prior art. In conventional systems sequence analysis is a sequential process: one iteration of the algorithm must complete before the next iteration may be performed. In contrast, embodiments of the inventive concept permit parallel execution of multiple comparisons in determining the preferred selection of the longest continuous match at each step. While embodiments of the inventive concept might perform more comparisons overall than conventional sequence analysis, by providing parallel execution paths overall time required to perform sequence analysis is reduced. In addition, embodiments of the inventive concept may be implemented using FPGAs attached to SSDs: by implementing the sequence analysis within such FPGAs, performance is improved as there is no need to transfer potentially large amounts of data from the storage device to the host computer memory to perform the algorithm. Processing may be performed locally by the FPGA with its own fast access to data stored on the SSD (faster than transferring data to the host memory). Such embodiments of the inventive concept also free up the host processor to perform other tasks than perform the sequence analysis, reducing the use of host resources.

The following discussion is intended to provide a brief, general description of a suitable machine or machines in which certain aspects of the inventive concept may be implemented. The machine or machines may be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines may include embedded controllers, such as programmable or non-programmable logic devices or arrays, application-specific integrated circuits (ASICs), embedded computers, smart cards, and the like. The machine or machines may utilize one or more connections to one or more remote machines, such as through a network interface, modem, or other communicative coupling. Machines may be interconnected by way of a physical and/or logical network, such as an intranet, the Internet, local area networks, wide area networks, etc. One skilled in the art will appreciate that network communication may utilize various wired and/or wireless short range or long range carriers and protocols, including radio frequency (RF), satellite, microwave, Institute of Electrical and Electronics Engineers (IEEE) 802.11, Bluetooth®, optical, infrared, cable, laser, etc.

Embodiments of the present inventive concept may be described by reference to or in conjunction with associated data including functions, procedures, data structures, application programs, etc. which when accessed by a machine results in the machine performing tasks or defining abstract data types or low-level hardware contexts. Associated data may be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data may be delivered over transmission environments, including the physical and/or logical network, in the form of packets, serial data, parallel data, propagated signals, etc., and may be used in a compressed or encrypted format. Associated data may be used in a distributed environment, and stored locally and/or remotely for machine access.

Embodiments of the inventive concept may include a tangible, non-transitory machine-readable medium comprising instructions executable by one or more processors, the instructions comprising instructions to perform the elements of the inventive concepts as described herein. The various operations of methods described above may be performed by any suitable means capable of performing the operations, such as various hardware and/or software component(s), circuits, and/or module(s). The software may comprise an ordered listing of executable instructions for implementing logical functions, and may be embodied in any "processor-readable medium" for use by or in connection with an instruction execution system, apparatus, or device, such as a single or multiple-core processor or processor-containing system.

The blocks or steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art.

Having described and illustrated the principles of the inventive concept with reference to illustrated embodiments, it will be recognized that the illustrated embodiments may be modified in arrangement and detail without departing from such principles, and may be combined in any desired manner. And, although the foregoing discussion has focused on particular embodiments, other configurations are contemplated. In particular, even though expressions such as "according to an embodiment of the inventive concept" or the like are used herein, these phrases are meant to generally reference embodiment possibilities, and are not intended to limit the inventive concept to particular embodiment configurations. As used herein, these terms may reference the same or different embodiments that are combinable into other embodiments.

The foregoing illustrative embodiments are not to be construed as limiting the inventive concept thereof. Although a few embodiments have been described, those skilled in the art will readily appreciate that many modifications are possible to those embodiments without materially departing from the novel teachings and advantages of the present disclosure. Accordingly, all such modifications are intended to be included within the scope of this inventive concept as defined in the claims.

Embodiments of the inventive concept may extend to the following statements, without limitation:

Statement 1. An embodiment of the inventive concept includes a solid state drive (SSD), comprising:

flash memory to store data;

an SSD controller to manage reading data from and writing data to the flash memory;

a field programmable gate array (FPGA) operative to perform a comparison of a search sequence with a reference sequence, the reference sequence stored in the flash memory, the FPGA operative to:

identify a continuous match of atoms between the search sequence and the reference sequence;

divide the search sequence into a left portion of the search sequence that includes first atoms before the continuous match of atoms in the search sequence, a center portion of the search sequence that includes the continuous match of atoms in the search sequence, and a right portion of the search sequence that includes second atoms after the continuous match of atoms in the search sequence;

match the left portion of the search sequence with the reference sequence; and match the right portion of the search sequence with the reference sequence.

Statement 2. An embodiment of the inventive concept includes the SSD according to statement 1, wherein the continuous match of atoms includes a longest continuous match of atoms.

Statement 3. An embodiment of the inventive concept includes the SSD according to statement 1, wherein:

the first atoms before the continuous match of atoms in the search sequence includes all atoms before the continuous match of atoms in the search sequence; and the second atoms after the continuous match of atoms in the search sequence includes all atoms after the continuous match of atoms in the search sequence.

Statement 4. An embodiment of the inventive concept includes the SSD according to statement 1, wherein the FPGA is operative to:

recursively match the left portion of the search sequence with the reference sequence; and recursively match the right portion of the search sequence with the reference sequence.

Statement 5. An embodiment of the inventive concept includes the SSD according to statement 1, wherein the FPGA is further operative to:

match the left portion of the search sequence with a left portion of the reference sequence; and match the right portion of the search sequence with a right portion of the reference sequence.

Statement 6. An embodiment of the inventive concept includes the SSD according to statement 1, wherein the FPGA is further operative to match the left portion of the search sequence with the reference sequence in parallel with matching the right portion of the search sequence with the reference sequence.

Statement 7. An embodiment of the inventive concept includes the SSD according to statement 1, wherein the FPGA is further operative to:

compare a plurality of subsequences of atoms in the search sequence with a plurality of starting locations in the reference sequence; and select a first subsequence of atoms in the search sequence that includes the continuous match of atoms.

Statement 8. An embodiment of the inventive concept includes the SSD according to statement 7, wherein the atoms are drawn from a set including nucleotides, amino acids, letters, words, and pixel values.

Statement 9. An embodiment of the inventive concept includes the SSD according to statement 7, wherein the FPGA is further operative to compare the plurality of subsequences of atoms in the search sequence with the plurality of starting locations in the reference sequence in parallel.

Statement 10. An embodiment of the inventive concept includes the SSD according to statement 7, wherein the FPGA is further operative to:

assign a weight to each comparison of the plurality of subsequences of atoms in the search sequence with the plurality of starting locations in the reference sequence, each weight based on a length of the subsequence of atoms in the search sequence and a location in the reference sequence; and determine a weighted match for each comparison of the plurality of subsequences of atoms in the search sequence with the plurality of starting locations in the reference sequence, the weighted match based on the weight and a number of continuous atoms in the subsequence that match continuous atoms in the reference sequence; and select the first subsequence of atoms in the search sequence that includes a highest weighted match.

Statement 11. An embodiment of the inventive concept includes the SSD according to statement 10, wherein the weights assigned to the plurality of comparisons are drawn from a set including center match weights, left match weights, and right match weights.

Statement 12. An embodiment of the inventive concept includes the SSD according to statement 10, wherein the weight assigned to each comparison is not unique.

Statement 13. An embodiment of the inventive concept includes the method according to statement 7, wherein the plurality of subsequences of atoms includes the plurality of subsequences of atoms either starting at a first atom in the search sequence or ending at a last atom in the search sequence.

Statement 14. An embodiment of the inventive concept includes the SSD according to statement 7, wherein the FPGA is further operative to:

assign a weight to a comparison of a first atom in the search sequence and a second atom in the reference sequence, the weight reflecting a similarity between the first atom in the search sequence and the second atom in the reference sequence; and select the first subsequence of atoms in the search sequence based on the length of the continuous match and the weight assigned to the comparison of the first atom in the search sequence and the second atom in the reference sequence.

Statement 15. An embodiment of the inventive concept includes a method, comprising:

receiving a reference sequence and a search sequence, the reference sequence including a first sequence of atoms, the search sequence including a second sequence of atoms;

identifying a continuous match of atoms between the search sequence and the reference sequence;

dividing the search sequence into a left portion of the search sequence that includes first atoms before the continuous match of atoms in the search sequence, a center portion of the search sequence that includes the continuous match of atoms in the search sequence, and a right portion of the search sequence that includes second atoms after the continuous match of atoms in the search sequence;

matching the left portion of the search sequence with the reference sequence; and matching the right portion of the search sequence with the reference sequence.

Statement 16. An embodiment of the inventive concept includes the method according to statement 15, wherein the continuous match of atoms includes a longest continuous match of atoms.

Statement 17. An embodiment of the inventive concept includes the method according to statement 15, wherein:

the first atoms before the continuous match of atoms in the search sequence includes all atoms before the continuous match of atoms in the search sequence; and the second atoms after the continuous match of atoms in the search sequence includes all atoms after the continuous match of atoms in the search sequence.

Statement 18. An embodiment of the inventive concept includes the method according to statement 15, wherein the FPGA is operative to:

matching the left portion of the search sequence with the reference sequence includes recursively matching the left portion of the search sequence with the reference sequence; and matching the right portion of the search sequence with the reference sequence includes recursively matching the right portion of the search sequence with the reference sequence.

Statement 19. An embodiment of the inventive concept includes the method according to statement 15, wherein:

matching the left portion of the search sequence with the reference sequence includes matching the left portion of the search sequence with a left portion of the reference sequence; and matching the right portion of the search sequence with the reference sequence includes matching the right portion of the search sequence with a right portion of the reference sequence.

Statement 20. An embodiment of the inventive concept includes the method according to statement 15, wherein:

matching the left portion of the search sequence with the reference sequence includes matching the left portion of the search sequence with the reference sequence based at least in part on the left portion of the search sequence including at least one atom; and matching the right portion of the search sequence with the reference sequence includes matching the right portion of the search sequence with the reference sequence based at least in part on the right portion of the search sequence including at least one atom.

Statement 21. An embodiment of the inventive concept includes the method according to statement 15, wherein matching the right portion of the search sequence with the reference sequence includes matching the right portion of the search sequence with the reference sequence in parallel with matching the left portion of the search sequence with the reference sequence.

Statement 22. An embodiment of the inventive concept includes the method according to statement 15, wherein identifying a continuous match of atoms between the search sequence and the reference sequence includes:

performing a comparison of a plurality of subsequences of atoms in the search sequence with a plurality of starting locations in the reference sequence; and selecting a first subsequence of atoms in the search sequence that includes the continuous match of atoms.

Statement 23. An embodiment of the inventive concept includes the method according to statement 22, wherein performing a comparison of a plurality of subsequences of atoms in the search sequence with a plurality of location positions in the reference sequence includes performing the comparison of the plurality of subsequences of atoms in the search sequence with the plurality of location positions in the reference sequence in parallel.

Statement 24. An embodiment of the inventive concept includes the method according to statement 22, wherein:

performing a comparison of a plurality of subsequences of atoms in the search sequence with a plurality of starting locations in the reference sequence includes, for each comparison:

assigning a weight, each weight based on a length of the subsequence of atoms in the search sequence and a location in the reference sequence; and determining a weighted match, the weighted match based on the weight and a number of continuous atoms in the subsequence that match continuous atoms in the reference sequence; and selecting a first subsequence of atoms in the search sequence that includes the continuous match of atoms includes selecting the first subsequence of atoms in the search sequence that includes a highest weighted match.

Statement 25. An embodiment of the inventive concept includes the method according to statement 24, wherein the weights assigned to every comparison are drawn from a set including center match weights, left match weights, and right match weights.

Statement 26. An embodiment of the inventive concept includes the method according to statement 24, wherein the weight assigned to each comparison is not unique.

Statement 27. An embodiment of the inventive concept includes the method according to statement 22, wherein the plurality of subsequences of atoms includes the plurality of subsequences of atoms either starting at a first atom in the search sequence or ending at a last atom in the search sequence.

Statement 28. An embodiment of the inventive concept includes the method according to statement 22, wherein:

identifying a continuous match of atoms between the search sequence and the reference sequence further includes assigning a weight to a comparison of a first atom in the search sequence and a second atom in the reference sequence, the weight reflecting a similarity between the first atom in the search sequence and the second atom in the reference sequence; and selecting a first subsequence of atoms in the search sequence that includes the continuous match of atoms includes selecting the first subsequence of atoms in the search sequence based on the length of the continuous match and the weight assigned to the comparison of the first atom in the search sequence and the second atom in the reference sequence.

Statement 29. An embodiment of the inventive concept includes the method according to statement 15, wherein the reference sequence is a reference genetic sequence and the search sequence is a search genetic sequence.

Statement 30. An embodiment of the inventive concept includes the method according to statement 15, wherein the reference sequence is a reference text sequence and the search sequence is a search text sequence.

Statement 31. An embodiment of the inventive concept includes the method according to statement 15, wherein the reference sequence is a reference amino acid sequence and the search sequence is a search amino acid sequence.

Statement 32. An embodiment of the inventive concept includes the method according to statement 15, wherein the reference sequence is a reference pixel sequence and the search sequence is a search pixel sequence.

Statement 33. An embodiment of the inventive concept includes an article, comprising a non-transitory storage medium, the non-transitory storage medium having stored thereon instructions that, when executed by a machine, result in:

receiving a reference sequence and a search sequence, the reference sequence including a first sequence of atoms, the search sequence including a second sequence of atoms;

identifying a continuous match of atoms between the search sequence and the reference sequence;

dividing the search sequence into a left portion of the search sequence that includes first atoms before the continuous match of atoms in the search sequence, a center portion of the search sequence that includes the continuous match of atoms in the search sequence, and a right portion of the search sequence that includes second atoms after the continuous match of atoms in the search sequence;

matching the left portion of the search sequence with the reference sequence; and matching the right portion of the search sequence with the reference sequence.

Statement 34. An embodiment of the inventive concept includes the article according to statement 33, wherein the continuous match of atoms includes a longest continuous match of atoms.

Statement 35. An embodiment of the inventive concept includes the article according to statement 33, wherein:

the first atoms before the continuous match of atoms in the search sequence includes all atoms before the continuous match of atoms in the search sequence; and the second atoms after the continuous match of atoms in the search sequence includes all atoms after the continuous match of atoms in the search sequence.

Statement 36. An embodiment of the inventive concept includes the article according to statement 33, wherein the FPGA is operative to:

matching the left portion of the search sequence with the reference sequence includes recursively matching the left portion of the search sequence with the reference sequence; and matching the right portion of the search sequence with the reference sequence includes recursively matching the right portion of the search sequence with the reference sequence.

Statement 37. An embodiment of the inventive concept includes the article according to statement 33, wherein:

matching the left portion of the search sequence with the reference sequence includes matching the left portion of the search sequence with a left portion of the reference sequence; and matching the right portion of the search sequence with the reference sequence includes matching the right portion of the search sequence with a right portion of the reference sequence.

Statement 38. An embodiment of the inventive concept includes the article according to statement 33, wherein:

matching the left portion of the search sequence with the reference sequence includes matching the left portion of the search sequence with the reference sequence based at least in part on the left portion of the search sequence including at least one atom; and matching the right portion of the search sequence with the reference sequence includes matching the right portion of the search sequence with the reference sequence based at least in part on the right portion of the search sequence including at least one atom.

Statement 39. An embodiment of the inventive concept includes the article according to statement 33, wherein matching the right portion of the search sequence with the reference sequence includes matching the right portion of the search sequence with the reference sequence in parallel with matching the left portion of the search sequence with the reference sequence.

Statement 40. An embodiment of the inventive concept includes the article according to statement 33, wherein identifying a continuous match of atoms between the search sequence and the reference sequence includes:

performing a comparison of a plurality of subsequences of atoms in the search sequence with a plurality of starting locations in the reference sequence; and selecting a first subsequence of atoms in the search sequence that includes the continuous match of atoms.

Statement 41. An embodiment of the inventive concept includes the article according to statement 40, wherein performing a comparison of a plurality of subsequences of atoms in the search sequence with a plurality of location positions in the reference sequence includes performing the comparison of the plurality of subsequences of atoms in the search sequence with the plurality of location positions in the reference sequence in parallel.

Statement 42. An embodiment of the inventive concept includes the article according to statement 40, wherein:

performing a comparison of a plurality of subsequences of atoms in the search sequence with a plurality of starting locations in the reference sequence includes, for each comparison:

assigning a weight, each weight based on a length of the subsequence of atoms in the search sequence and a location in the reference sequence; and determining a weighted match, the weighted match based on the weight and a number of continuous atoms in the subsequence that match continuous atoms in the reference sequence; and selecting a first subsequence of atoms in the search sequence that includes the continuous match of atoms includes selecting the first subsequence of atoms in the search sequence that includes a highest weighted match.

Statement 43. An embodiment of the inventive concept includes the article according to statement 42, wherein the weights assigned to every comparison are drawn from a set including center match weights, left match weights, and right match weights.

Statement 44. An embodiment of the inventive concept includes the article according to statement 42, wherein the weight assigned to each comparison is not unique.

Statement 45. An embodiment of the inventive concept includes the article according to statement 40, wherein the plurality of subsequences of atoms includes the plurality of subsequences of atoms either starting at a first atom in the search sequence or ending at a last atom in the search sequence.

Statement 46. An embodiment of the inventive concept includes the article according to statement 40, wherein:

identifying a continuous match of atoms between the search sequence and the reference sequence further includes assigning a weight to a comparison of a first atom in the search sequence and a second atom in the reference sequence, the weight reflecting a similarity between the first atom in the search sequence and the second atom in the reference sequence; and selecting a first subsequence of atoms in the search sequence that includes the continuous match of atoms includes selecting the first subsequence of atoms in the search sequence based on the length of the continuous match and the weight assigned to the comparison of the first atom in the search sequence and the second atom in the reference sequence.

Statement 47. An embodiment of the inventive concept includes the article according to statement 33, wherein the reference sequence is a reference genetic sequence and the search sequence is a search genetic sequence.

Statement 48. An embodiment of the inventive concept includes the article according to statement 33, wherein the reference sequence is a reference text sequence and the search sequence is a search text sequence.

Statement 49. An embodiment of the inventive concept includes the article according to statement 33, wherein the reference sequence is a reference amino acid sequence and the search sequence is a search amino acid sequence.

Statement 50. An embodiment of the inventive concept includes the article according to statement 33, wherein the reference sequence is a reference pixel sequence and the search sequence is a search pixel sequence.

Consequently, in view of the wide variety of permutations to the embodiments described herein, this detailed description and accompanying material is intended to be illustrative only, and should not be taken as limiting the scope of the inventive concept. What is claimed as the inventive concept, therefore, is all such modifications as may come within the scope and spirit of the following claims and equivalents thereto.

What is claimed is:

1. A solid state drive (SSD), comprising:
flash memory to store data;
an SSD controller to manage reading data from and writing data to the flash memory;
a field programmable gate array (FPGA) operative to perform a comparison of a search sequence with a reference sequence, the reference sequence stored in the flash memory, the FPGA configured to:
identify a continuous match of atoms between the search sequence and the reference sequence;
divide the search sequence into a left portion of the search sequence that includes first atoms before the continuous match of atoms in the search sequence, a center portion of the search sequence that includes the continuous match of atoms in the search sequence, and a right portion of the search sequence that includes second atoms after the continuous match of atoms in the search sequence, wherein there is a first gap between the left portion and the center portion in the reference sequence and a second gap between the center portion and the right portion in the reference sequence;
match the left portion of the search sequence with the reference sequence; and
match the right portion of the search sequence with the reference sequence,
wherein the FPGA may be reconfigured to match two different types of search sequences and reference sequences.

2. The SSD according to claim 1, wherein the FPGA is further configured to match the left portion of the search sequence with the reference sequence in parallel with matching the right portion of the search sequence with the reference sequence.

3. The SSD according to claim 1, wherein the FPGA is further configured to:
compare a plurality of subsequences of atoms in the search sequence with a plurality of starting locations in the reference sequence; and
select a first subsequence of atoms in the search sequence that includes the continuous match of atoms.

4. The SSD according to claim 3, wherein the FPGA is further configured to compare the plurality of subsequences of atoms in the search sequence with the plurality of starting locations in the reference sequence in parallel.

5. The SSD according to claim 3, wherein the FPGA is further configured to:
assign a weight to each comparison of the plurality of subsequences of atoms in the search sequence with the plurality of starting locations in the reference sequence, each weight based on a length of the subsequence of atoms in the search sequence and a location in the reference sequence;
determine a score for each comparison of the plurality of subsequences of atoms in the search sequence with the plurality of starting locations in the reference sequence, the score based on the weight and a number of continuous atoms in the subsequence that match continuous atoms in the reference sequence; and
select the first subsequence of atoms in the search sequence that includes a highest score.

6. The SSD according to claim 5, wherein the weights assigned to the plurality of comparisons are drawn from a set including center match weights, left match weights, and right match weights.

7. The SSD according to claim 3, wherein the FPGA is further configured to:
assign a weight to a comparison of a first atom in the search sequence and a second atom in the reference sequence, the weight reflecting a similarity between the first atom in the search sequence and the second atom in the reference sequence; and
select the first subsequence of atoms in the search sequence based on a length of the continuous match of atoms and the weight assigned to the comparison of the first atom in the search sequence and the second atom in the reference sequence.

8. A method, comprising:
receiving a reference sequence and a search sequence at a Field Programmable Gate Array (FPGA), the reference sequence including a first sequence of atoms, the search sequence including a second sequence of atoms;
identifying a continuous match of atoms between the search sequence and the reference sequence by the FPGA;
dividing the search sequence into a left portion of the search sequence that includes first atoms before the continuous match of atoms in the search sequence, a center portion of the search sequence that includes the continuous match of atoms in the search sequence, and a right portion of the search sequence that includes second atoms after the continuous match of atoms in the search sequence, wherein there is a first gap between the left portion and the center portion in the reference sequence and a second gap between the center portion and the right portion in the reference sequence;

matching the left portion of the search sequence with the reference sequence by the FPGA; and matching the right portion of the search sequence with the reference sequence by the FPGA, wherein the FPGA may be reconfigured to match two different types of search sequences and reference sequences.

9. The method according to claim 8, wherein matching the right portion of the search sequence with the reference sequence includes matching the right portion of the search sequence with the reference sequence in parallel with matching the left portion of the search sequence with the reference sequence.

10. The method according to claim 8, wherein identifying a continuous match of atoms between the search sequence and the reference sequence includes:

performing a comparison of a plurality of subsequences of atoms in the search sequence with a plurality of starting locations in the reference sequence; and selecting a first subsequence of atoms in the search sequence that includes the continuous match of atoms.

11. The method according to claim 10, wherein performing a comparison of a plurality of subsequences of atoms in the search sequence with a plurality of location positions in the reference sequence includes performing the comparison of the plurality of subsequences of atoms in the search sequence with the plurality of location positions in the reference sequence in parallel.

12. The method according to claim 10, wherein:

performing a comparison of a plurality of subsequences of atoms in the search sequence with a plurality of starting locations in the reference sequence includes, for each comparison:

assigning a weight, each weight based on a length of the subsequence of atoms in the search sequence and a location in the reference sequence; and determining a score, the score based on the weight and a number of continuous atoms in the subsequence that match continuous atoms in the reference sequence; and selecting a first subsequence of atoms in the search sequence that includes the continuous match of atoms includes selecting the first subsequence of atoms in the search sequence that includes a highest score.

13. The method according to claim 12, wherein the weights assigned to every comparison are drawn from a set including center match weights, left match weights, and right match weights.

14. The method according to claim 10, wherein:

identifying a continuous match of atoms between the search sequence and the reference sequence further includes assigning a weight to a comparison of a first atom in the search sequence and a second atom in the reference sequence, the weight reflecting a similarity between the first atom in the search sequence and the second atom in the reference sequence; and selecting a first subsequence of atoms in the search sequence that includes the continuous match of atoms includes selecting the first subsequence of atoms in the search sequence based on a length of the continuous match of atoms and the weight assigned to the comparison of the first atom in the search sequence and the second atom in the reference sequence.

15. The method according to claim 8, wherein:

the reference sequence is a reference multi-word text sequence and the search sequence is a multi-word search text sequence;

the reference sequence is a reference amino acid sequence and the search sequence is a search amino acid sequence; or the reference sequence is a reference pixel sequence and the search sequence is a search pixel sequence.

16. An article, comprising a non-transitory storage medium, the non-transitory storage medium having stored thereon instructions that, when executed by a Field Programmable Gate Array (FPGA), result in:

receiving a reference sequence and a search sequence at the FPGA, the reference sequence including a first sequence of atoms, the search sequence including a second sequence of atoms;

identifying a continuous match of atoms between the search sequence and the reference sequence by the FPGA;

dividing the search sequence into a left portion of the search sequence that includes first atoms before the continuous match of atoms in the search sequence, a center portion of the search sequence that includes the continuous match of atoms in the search sequence, and a right portion of the search sequence that includes second atoms after the continuous match of atoms in the search sequence, wherein there is a first gap between the left portion and the center portion in the reference sequence and a second gap between the center portion and the right portion in the reference sequence;

matching the left portion of the search sequence with the reference sequence by the FPGA; and matching the right portion of the search sequence with the reference sequence by the FPGA, wherein the FPGA may be reconfigured to match two different types of search sequences and reference sequences.

17. The article according to claim 16, wherein matching the right portion of the search sequence with the reference sequence includes matching the right portion of the search sequence with the reference sequence in parallel with matching the left portion of the search sequence with the reference sequence.

18. The article according to claim 16, wherein identifying a continuous match of atoms between the search sequence and the reference sequence includes:

performing a comparison of a plurality of subsequences of atoms in the search sequence with a plurality of starting locations in the reference sequence; and selecting a first subsequence of atoms in the search sequence that includes the continuous match of atoms.

19. The article according to claim 18, wherein:

performing a comparison of a plurality of subsequences of atoms in the search sequence with a plurality of starting locations in the reference sequence includes, for each comparison:

assigning a weight, each weight based on a length of the subsequence of atoms in the search sequence and a location in the reference sequence; and determining a score, the score based on the weight and a number of continuous atoms in the subsequence that match continuous atoms in the reference sequence; and selecting a first subsequence of atoms in the search sequence that includes the continuous match of atoms includes selecting the first subsequence of atoms in the search sequence that includes a highest score.

20. The article according to claim 18, wherein:
identifying a continuous match of atoms between the search sequence and the reference sequence further includes assigning a weight to a comparison of a first atom in the search sequence and a second atom in the reference sequence, the weight reflecting a similarity between the first atom in the search sequence and the second atom in the reference sequence; and
selecting a first subsequence of atoms in the search sequence that includes the continuous match of atoms includes selecting the first subsequence of atoms in the search sequence based on a length of the continuous match of atoms and the weight assigned to the comparison of the first atom in the search sequence and the second atom in the reference sequence.

21. The SSD according to claim 1, wherein the FPGA is configured to:
match the left portion of the search sequence with the reference sequence recursively; and
match the right portion of the search sequence with the reference sequence recursively.

22. The method according to claim 8, wherein the two different types are drawn from a set including nucleotides, amino acids, multi-word sequences, or pixel values.

\* \* \* \* \*